(12) United States Patent
Cook et al.

(10) Patent No.: US 7,018,991 B2
(45) Date of Patent: *Mar. 28, 2006

(54) 17β-AMINO AND HYDROXYLAMINO-11 β-ARYLSTEROIDS AND THEIR DERIVATIVES HAVING AGONIST OR ANTAGONIST HORMONAL PROPERTIES

(75) Inventors: C. Edgar Cook, Staunton, VA (US); John A. Kepler, Raleigh, NC (US); Gary S. Bartley, Durham, NC (US); Rupa S. Shetty, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/611,785

(22) Filed: Jul. 2, 2003

(65) Prior Publication Data

US 2004/0023936 A1    Feb. 5, 2004

Related U.S. Application Data

(60) Continuation of application No. 09/895,395, filed on Jul. 2, 2001, now Pat. No. 6,620,801, and a division of application No. 09/086,560, filed on May 29, 1998, now Pat. No. 6,262,042.

(51) Int. Cl.
*A61P 15/00* (2006.01)
*A61K 31/56* (2006.01)
*A61K 31/58* (2006.01)
*C07J 41/00* (2006.01)

(52) U.S. Cl. ............... 514/169; 514/176; 514/177; 540/106

(58) Field of Classification Search ............... 514/169, 514/176, 177; 540/106
See application file for complete search history.

(56) References Cited

U.S. PATENT DOCUMENTS

| | | | |
|---|---|---|---|
| 4,386,085 A | 5/1983 | Teutsch et al. | 424/238 |
| 4,447,424 A | 5/1984 | Teutsch et al. | 424/238 |
| 4,477,445 A | 10/1984 | Philibert et al. | |
| 4,481,144 A | 11/1984 | Varma | 260/397.45 |
| 4,529,548 A | 7/1985 | Varma et al. | 260/397.45 |
| 4,609,651 A | 9/1986 | Rohde et al. | 514/179 |
| 4,774,236 A | 9/1988 | Cook et al. | 514/176 |
| 4,861,763 A | 8/1989 | Cook et al. | 514/172 |
| 4,871,724 A | 10/1989 | Groen et al. | 514/173 |
| 4,874,754 A | 10/1989 | Nique et al. | 514/178 |
| 4,900,725 A | 2/1990 | Nique et al. | 514/173 |
| 4,954,490 A | 9/1990 | Cook et al. | 514/176 |
| 5,073,548 A | 12/1991 | Cook et al. | 514/169 |
| 5,962,444 A | 10/1999 | Cook et al. | 514/177 |
| 6,015,805 A | 1/2000 | Cook et al. | 514/176 |
| 6,020,328 A | 2/2000 | Cook et al. | 514/176 |
| 6,043,235 A | 3/2000 | Cook et al. | 514/173 |
| 6,093,707 A | 7/2000 | Cook et al. | 514/172 |
| 6,172,052 B1 | 1/2001 | Cook et al. | 514/169 |
| 6,262,042 B1 | 7/2001 | Cook et al. | 514/177 |
| 6,620,801 B1 | 9/2003 | Cook et al. | 514/173 |

FOREIGN PATENT DOCUMENTS

| | | |
|---|---|---|
| DE | 287 510 | 2/1991 |
| DE | 289 539 | 5/1991 |
| DE | 290 198 | 5/1991 |
| EP | 0 057 115 | 8/1982 |
| EP | 0 116 974 | 8/1984 |
| EP | 0 147 361 | 7/1985 |
| EP | 0 0190 759 | 8/1986 |
| EP | 0 192 598 | 8/1986 |
| EP | 0 245 170 | 11/1987 |
| EP | 0 254 670 | 1/1988 |
| EP | 0 277 089 | 8/1988 |
| EP | 0 277 676 | 8/1988 |
| EP | 0 289 073 | 11/1988 |
| EP | 0 305 242 | 3/1989 |
| EP | 0 321 010 | 6/1989 |
| EP | 0 349 481 | 1/1990 |
| EP | 0 404 283 | 12/1990 |
| EP | 0 411 733 | 2/1991 |
| EP | 0 549 041 | 6/1993 |
| HU | 185158 B | 12/1984 |
| HU | 207341 B | 3/1993 |
| HU | 297 925 B * | 1/2002 |
| WO | WO 87/05908 | 10/1987 |
| WO | WO 88/01868 | 3/1988 |
| WO | WO 89/12448 | 12/1989 |
| WO | WO 92/11279 | 7/1992 |
| WO | WO 93/17686 | 9/1993 |
| WO | WO 93/21926 | 11/1993 |
| WO | WO 96/30390 | 10/1996 |
| WO | WO 97/41145 | 11/1997 |

OTHER PUBLICATIONS

Chemical Abstract, AN 78501u, EP 299,913, Jan. 18, 1989.
Chemical Abstract, AN 6285s, FR 2,586,021, Feb. 13, 1987.
Chemical Abstract, AN 154227b, EP 308 345, Mar. 22, 1989.

(Continued)

*Primary Examiner*—Brenda Coleman
(74) *Attorney, Agent, or Firm*—Oblon, Spivak, McClelland, Maier & Neustadt, P.C.

(57) ABSTRACT

The invention is directed to a novel class of steroids which exhibit potent antiprogestational activity.

18 Claims, 3 Drawing Sheets

OTHER PUBLICATIONS

Chemical Abstract, AN 164959b, EP 310,542, Apr. 5, 1989.
Chemical Abstract, AN 132580a, EP 369,881, May. 23, 1990.
Chemical Abstract, AN 93429d, DE 3,621,024, Dec. 23, 1987.
G. Teutsch, et al., Human Reproduction, vol. 9, Supplement 1, pp. 12 to 31, "History and Perspectives of Antiprogestins From the Chemist's Point of View", 1994.
C.E. Cook, et al., Human Reproduction, vol. 9, Supplement 1, pp. 32 to 39, "Effects of D-Ring Substituents on Antiprogestational (Antagonist) and Progestational (Agonist) Activity of 11β-Aryl Steroids", 1994.
M.J. Van Den Heuvel, et al., Recueil des Travaux Shimiques des Pays-Bas, vol. 112, No. 02, pp. 107 to 112, "Synthesis of 6β-Methyl Analogues of Mifepristone, New Selective Antiprogestagens", 1993.
Balasubramanian et al., Recent Developments IN Cancer Cytotoxics, Annual Reports in Medicinal Chemistry, vol. 33, pp. 151-159, 1988.
Salmon et al., Principles of Cancer Therapy, Cecil Textbook of Medicine, 20th Edition, pp. 1036-1049, 1996.
U.S. Appl. No. 10/051,172, filed Jan. 22, 2002, Cook, et al.
U.S. Appl. No. 09/562,905, filed Aug. 8, 2000, Cook, et al.
U.S. Appl. No. 09/389,212, filed Sep. 3, 1999, Cook, et al.
U.S. Appl. No. 10/611,785, filed Jul. 2, 2003, Cook, et al.
Notification of Second Office Action from People's Republic of China (2pp.) w. *English Language Text of notification of second office action* (2pp.) 2005.

* cited by examiner a) NaBH₃CN b) CF₃COOH, H₂O, CH₂Cl₂

17β-AMINO AND HYDROXYLAMINO-11 β-ARYLSTEROIDS AND THEIR DERIVATIVES HAVING AGONIST OR ANTAGONIST HORMONAL PROPERTIES

BACKGROUND OF THE INVENTION

1. Field of the Invention

This invention relates to a novel class of 17β-amino and hydroxylamino steroids which are believed to bind to the progestin receptor and which exhibit potent antiprogestational activity, steroid intermediates which are useful for preparing same and methods for the preparation of steroid intermediates. Such compounds are useful for treatment of fibroids, endometriosis, and certain tumors, in causing cervical ripening prior to delivery, in hormone replacement therapy and in control of fertility and reproduction.

2. Discussion of the Background

Progesterone plays a major role in reproductive health and functioning. Its effects on, for example, the uterus, breast, cervix and hypothalamic-pituitary unit are well established. It also has extra-reproductive activities that are less well studied, such as effects on the brain, the immune system, the vascular endothelial system and on lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in treating a variety of disease states and conditions.

Steroid hormones exert their effects, in-part, by binding to intracellular receptors. Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature and their effects in vitro, in animals and in humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993). In view of the pivotal role that progesterone plays in reproduction, it is not surprising that antiprogestins could play a part in fertility control, including contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.

2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.

3. Treatment of endometriosis—this common (5 to 15% incidence, much larger in infertile women) and often painful condition is now treated with drugs such as danazol or gonadotrophin-releasing hormone analogs that have significant side-effects, or must be dealt with surgically.

4. Hormone replacement therapy, where they may be given to interupt or curtail the activity of progestins.

5. Cancers, particularly breast cancers—the presence of progestin receptors in many breast cancers has suggested the use of antiprogestins in treating metatstatic cancer or in prevention of recurrence or initial development of cancer.

6. Other tumors such as meningiomas—these brain membrane tumors, although non-malignant, result in death of the patient and nonsurgical treatments are lacking.

7. Male contraception—antiprogestins can interfere with sperm viability, although whether this is an antiprogestational effect or not is controversial, as it may relate to the antiglucocorticoid activity of such compounds.

8. Antiestrogenic effects—at least some antiprogestins oppose the action of estrogens in certain tests, but apparently through a mechanism that does not involve classical hormone receptors. This opens a variety of possibilities for their medical use.

9. Antiglucocorticoid effects—this is a common sideeffect of antiprogestins, which can be useful in some instances, such as the treatment of Cushing's syndrome, and could play a role in immune disorders, for example. In other instances it is desirable to minimize such effects.

The effects and uses of progesterone agonists have been well documented. In addition, it has been recently shown that certain compounds structurally related to the known antiprogestins have strong agonist activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Natl. Acad. Sci., 93, 8739–8744 (1996)). Thus the general class of antiprogestins can have subclasses, which may vary in their clinical profiles.

Generally antiprogestational activity has been associated with the presence of an 11β-aryl substituent on the steroid nucleus, together with a $\Delta^{4,9}$-3-ketone or $\Delta^4$-3-ketone moiety. However, it has been shown that substituents on the D-ring of the steroid can have a marked influence on the biological profile of these compounds (see above). The earliest antiprogestins were substituted with a 17β-hydroxyl group and various 17α-substituents. (See for example, Teutsch, Jean G.; Costerousse, Germain; Philibert, Daniel, and Deraedt, Roger. Novel steroids. U.S. Pat. No. 4,386,085. 1983; Philibert, Daniel; Teutsch, Jean G.; Costerousse, Germain, and Deraedt, Roger. 3-Keto-19-nor-Δ-4,9-steroids. U.S. Pat. No. 4,477,445. 1983; Teutsch, Jean G.; Pantin, Germain; Costerousse, Saint-Maurice; Daniel Philibert; La Varenne Saint Hilaire; Roger Deraedt, inventors. Steroid derivatives. Roussel Uclaf, assignee. U.S. Pat. No. 4,447, 424. 1984; Cook, C. Edgar; Tallent, C. Ray; Reel, Jerry R., and Wani, Mansukh C. 17α-(Substituted-methyl)-17β-hydroxy/esterified hydroxy steroids and pharmaceutical compositions containing them. U.S. Pat. No. 4,774,236 (1988) and U.S. Pat. No. 4,861,763 (1989)). Then it was discovered that a 17β-acetyl, 17α-acyloxy group could also generate antiprogestational effects (Cook, C. Edgar; Lee, Y.-W.; Reel, Jerry R.; Wani, Mansukh C., Rector, Douglas. 11β-Substituted Progesterone Analogs. U.S. Pat. No. 4,954,490 (1990) and U.S. Pat. No. 5,073,548 (1991)), and various permutations of these findings have been made as well. However, introduction of a 16α-ethyl group or a hydrogen substituent at the 17α-position in the 17β-acyl series of compounds leads to agonist or partial agonist activity (C. E. Cook et al., Life Sciences, 52, 155–162 (1993)). Thus changes in the D-ring of the steroid result in a wide variety of effects on the biological activity. Accordingly there remains a need for antiprogestin compounds which exhibit higher specificity.

It can be seen that the 17β-position of current antiprogestins has been characterized by substitution with a carbon or an oxygen atom. No reports have been made of the effect of nitrogen substituents such as amines, amine amides, and hydroxylamines in the 17β-position of 11β-aryl steroids on their hormonal or antihormonal activity. Until the current invention there existed no methods for their synthesis. Very few 17β-amino and hydroxylamino steroids and none with 11β-substitution have been reported in either the general chemical literature or in patents. Indeed, one of the few reports of this type of 17β-substitution (P. Kaspar and H. Witzel, J. Steroid. Biochem., 23: 259 (1985)) shows that this type of substitution in the estrogen field leads to compounds that are one or more orders of magnitude less potent (as measured by receptor binding or standard in vivo tests for estrogenicity) than the corresponding 17β-hydroxy compounds. One novel feature of the present invention is the finding that 17β-nitrogen substituents in 11β-aryl steroids result in compounds with good binding to the progestin receptor and with surprisingly potent antiprogestational activity, or with potent antiprogestational activity accompanied by some progestational activity. Another novel feature of the present invention is the finding that 17β-nitrogen substituents in 11β-aryl steroids result in compounds having unusual antiestrogenic activity.

In addition, this invention provides a group of novel 17,17-spiro cyclic tetrahydropyrrole steroids. Although a very few 17,17-spiro cyclic tetrahydropyrrole steroids are known (cf. Keana, John F. W.; Tamura, Toshinari; McMillen, Debra A., and Jost, Patricia C. Synthesis and characterization of a novel cholesterol nitroxide spin label. Application to the molecular organization of human high-density lipoprotein. J. Am. Chem. Soc. 1981; 103(16):4904–4912), these have been used to develop spin labels and not for their biological properties. No such compounds with 11β-aryl substituents have been reported. Again, a novel feature of the present invention is the finding that these compounds surprisingly bind well to the progestin receptor and exhibit antiprogestational activity.

It is therefore the purpose of the present invention to provide novel and potent progestin antagonists (antiprogestins) and mixed or partial progestin agonists, to provide methods for their medical use in mammals, including humans, and to provide methods for their synthesis.

In spite of the clinical promise of antiprogestins, as of May 1, 1998, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above.

It is therefore the purpose of the present invention to provide novel and potent progestin antagonists (antiprogestins) and mixed or partial progestin agonists, and to provide methods for their medical use in mammals, including humans.

SUMMARY OF THE INVENTION

This invention provides a group of novel 17β-amino and hydroxy amino steroids, which are characterized by 11β-substitution, particularly 11β-aryl substitution.

According to one embodiment of the present invention is a hormonal or antihormonal steroid compound of structure I,

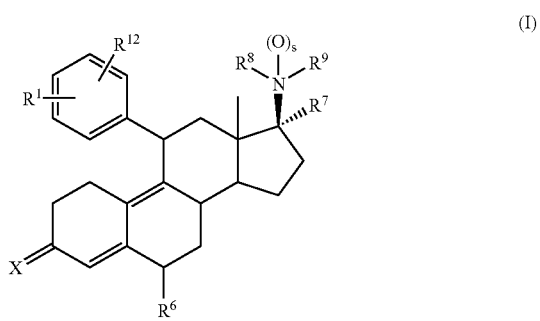

wherein $R^1$ is $(R^2R^3N(O)_r)$—, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ alkynyl, any of which may be optionally substituted; or

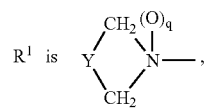

$R^1$ is where q is 0 or 1, Y is —$(CH_2)_m$— where m is an integer of 0 to 5, or Y is —$(CH_2)_n$-Z-$(CH_2)_p$— where n is an integer of 0 to 2, p is an integer of 0 to 2, and Z is a heteroatom (optionally substituted) and where the $CH_2$ groups may be optionally substituted; or $R^1$ is N-imidazolyl,-N-pyrrolyl-, H, halo-, HO—, $CF_3SO_2O$—, $C_{1-6}$ alkyl-O—, $C_{1-6}$ alkyl-S—, $C_{1-6}$ alkyl-S(O)—, $C_{1-6}$ alkyl-S($O_2$)—, $C_{1-6}$ alkyl-CO—, $C_{1-6}$ alkyl-CH(OH)—, NC—, HCC—, $C_6H_5CC$—, 2'-furyl, 3'-furyl, 2'-thiophenyl, 3'-thiophenyl, 2'-pyridyl, 3'-pyridyl, 4'-pyridyl, 2'-thiazolyl, 2'-N-methylimidazolyl, 5'-pyrimidinyl, $C_6H_5$—, $H_2C$=CH—, $C_{1-6}$ alkyl, or MeC(=$CH_2$)—;

$R^{12}$ is H or halo; or $R^1$ and $R^{12}$ combine to form a ring

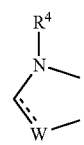

where W is $CH_2$, CH, NH, N, O, or S, and $R^4$ is H or $C_{1-6}$ alkyl;

X is O or NOR$^5$, where R$^5$ is H or C$_{1-6}$ alkyl, C$_{3-8}$ cycloalkyl, C$_{2-6}$ alkenyl, C$_{2-6}$ alkynyl, C$_{6-12}$ aryl, or heteroaryl, any of which may be optionally substituted; or X is (H, H), (H, OH), (H, OSi(C$_{1-6}$ alkyl)$_3$), or (H, OCOR$^5$), where R$^5$ is C$_{1-6}$ alkyl, C$_{3-8}$ cycloalkyl, C$_{2-6}$ alkenyl, C$_{2-6}$ alkynyl, C$_{6-12}$ aryl, aralkyl, aralkenyl, aralkynyl, heteroaryl, heteroaralkyl, heteroaralkenyl or heteroaralkynyl, any of which may be optionally substituted; or

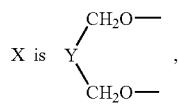

where Y is —(CH$_2$)$_m$— where m is an integer of 0 to 3, or Y is —(CH$_2$)$_n$-Z-(CH$_2$)$_p$— where n is an integer of 0 to 2, p is an integer of 0 to 2 and Z is a heteroatom (optionally substituted) or Z is a carbon atom substituted with one or two C$_{1-6}$ alkyl groups;

R$^6$ is H, C$_{1-6}$ alkyl or halogen;

R$^7$ is H, C$_{1-6}$ alkyl, C$_{2-6}$ alkenyl, C$_{2-6}$ alkynyl, C$_{3-8}$ cycloalkyl, C$_{6-12}$ aryl, aralkyl, aralkenyl, aralkynyl, heteroaryl, heteroaralkyl, heteroaralkenyl or heteroaralkynyl, any of which may be optionally substituted, CN, COOR$^{10}$ or CONHR$^{10}$, where R$^{10}$ is H, C$_{1-18}$ alkyl, C$_{2-18}$ alkenyl, C$_{2-18}$ alkynyl, C$_{3-8}$ cycloalkyl, C$_{6-12}$ aryl, aralkyl, aralkenyl, aralkynyl, heteroaryl, heteroaralkyl, heteroaralkenyl or heteroaralkynyl, any of which may be optionally substituted;

s is 0 or 1;

R$^8$ and R$^9$ are each independently H, C$_{1-6}$ alkyl, C$_{2-6}$ alkenyl or C$_{2-6}$ alkynyl, R$^{10}$CO, OR$^{11}$, any of which may be optionally substituted, where R$^{10}$ is H, C$_{1-18}$ alkyl, C$_{2-18}$ alkenyl, C$_{2-18}$ alkynyl, C$_{3-8}$ cycloalkyl, C$_{6-12}$ aryl, aralkyl, aralkenyl, aralkynyl, heteroaryl, heteroaralkyl, heteroaralkenyl or heteroaralkynyl any of which may be optionally substituted, and where R$^{11}$ is H, C$_{1-6}$ alkyl, Si(C$_{1-6}$ alkyl)$_3$, 2'-tetrahydropyranyl or R$^{10}$CO where R$^{10}$ is as defined above wherein when s is 0, R$^8$ may also be O$^-$ and R$^9$ is =CH$_2$ or =C(H, C$_{1-6}$), =C(H, aryl) or =C(C$_{1-6}$)$_2$ and the nitrogen attached to the 17-position is positively charged;

and pharmaceutically acceptable salts thereof.

According to another embodiment of the present invention is a hormonal or antihormonal steroid compound of structure II, (II)

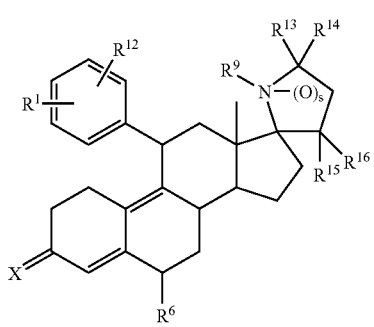

wherein
R$^1$ is (R$^2$R$^3$N(O)$_r$)—, where r is 0 or 1 and R$^2$ and R$^3$ are each independently H, C$_{1-6}$ alkyl, C$_{3-8}$ cycloalkyl, C$_{2-6}$ alkenyl or C$_{2-6}$ alkynyl, any of which may be optionally substituted; or

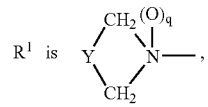

where q is 0 or 1, Y is —(CH$_2$)$_m$— where m is an integer of 0 to 5, or Y is —(CH$_2$)$_n$-Z-(CH$_2$)$_p$— where n is an integer of 0 to 2, p is an integer of 0 to 2, and Z is a heteroatom (optionally substituted) and where the CH$_2$ groups may be optionally substituted; or R$^1$ is N-imidazolyl,—N-pyrrolyl-, halo-, HO—, CF$_3$SO$_2$O—, C$_{1-6}$ alkyl O—, C$_{1-6}$ alkyl S—, C$_{1-6}$ alkyl S(O)—, C$_{1-6}$ alkyl S(O$_2$)—, C$_{1-6}$ alkyl CO—, C$_{1-6}$ alkyl CH(OH)—, NC—, HCC—, C$_6$H$_5$CC—, 2'-furyl, 3'-furyl, 2'-thiophenyl, 3'-thiophenyl, 2'-pyridyl, 3'-pyridyl, 4'-pyridyl, 2'-thiazolyl, 2'-N-methylimidazolyl, 5'-pyrimidinyl, C$_6$H$_5$—, H$_2$C=CH—, C$_{1-6}$ alkyl, or MeC(=CH$_2$)—;

R$^{12}$ is H or halo; or

R$^1$ and R$^{12}$ combine to form a ring

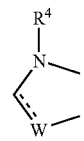

where W is CH$_2$, CH, NH, N, O, or S, and R$^4$ is H or C$_{1-6}$ alkyl;

X is O or NOR$^5$, where R$^5$ is H or C$_{1-6}$ alkyl, C$_{3-8}$ cycloalkyl, C$_{2-6}$ alkenyl, C$_{2-6}$ alkynyl, C$_{6-12}$ aryl, or heteroaryl, any of which may be optionally substituted; or X is (H, H), (H, OH), (H, OSi(C$_{1-6}$ alkyl)$_3$), or (H, OCOR$^5$), where R$^5$ is C$_{1-6}$ alkyl, C$_{3-8}$ cycloalkyl, C$_{2-6}$ alkenyl, C$_{2-6}$ alkynyl, C$_{6-12}$ aryl, aralkyl, aralkenyl, aralkynyl, heteroaryl, heteroaralkyl, heteroaralkenyl or heteroaralkynyl, any of which may be optionally substituted; or

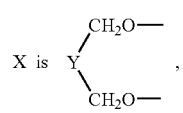

where Y is —(CH$_2$)$_m$— where m is an integer of 0 to 3, or Y is —(CH$_2$)$_n$-Z-(CH$_2$)$_p$— where n is an integer of 0 to 2, p is an integer of 0 to 2 and Z is a heteroatom (optionally substituted) or Z is a carbon atom substituted with one or two C$_{1-6}$ alkyl groups;

R$^6$ is H, C$_{1-6}$ alkyl or halogen;

s is 0 or 1;

R$^9$ is H, C$_{1-6}$ alkyl, C$_{2-6}$ alkenyl or C$_{2-6}$ alkynyl, R$^{10}$CO, OR$^{11}$, any of which may be optionally substituted, where R$^{10}$ is H, C$_{1-18}$ alkyl, C$_{2-18}$ alkenyl, C$_{2-18}$ alkynyl, C$_{3-8}$ cycloalkyl, C$_{6-12}$ aryl, aralkyl, aralkenyl, aralkynyl, heteroaryl, heteroaralkyl, heteroaralkenyl or heteroaralkynyl any of which may be optionally substituted, and where $R^{11}$ is H, $C_{1-6}$ alkyl, $Si(C_{1-6}$ alkyl$)_3$, 2'-tetrahydropyranyl or $R^{10}CO$ where $R^{10}$ is as defined above;

$R^{13}$ and $R^{14}$ are each independently H, $C_{1-18}$ alkyl, $C_{2-18}$ alkenyl, $C_{2-18}$ alkynyl, $C_{3-8}$ cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; or $R^{13}R^{14}$ is O; and $R^{15}$ and $R^{16}$ are each H or combine to form a group $=CH_2$, optionally substituted, and pharmaceutically acceptable salts thereof.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
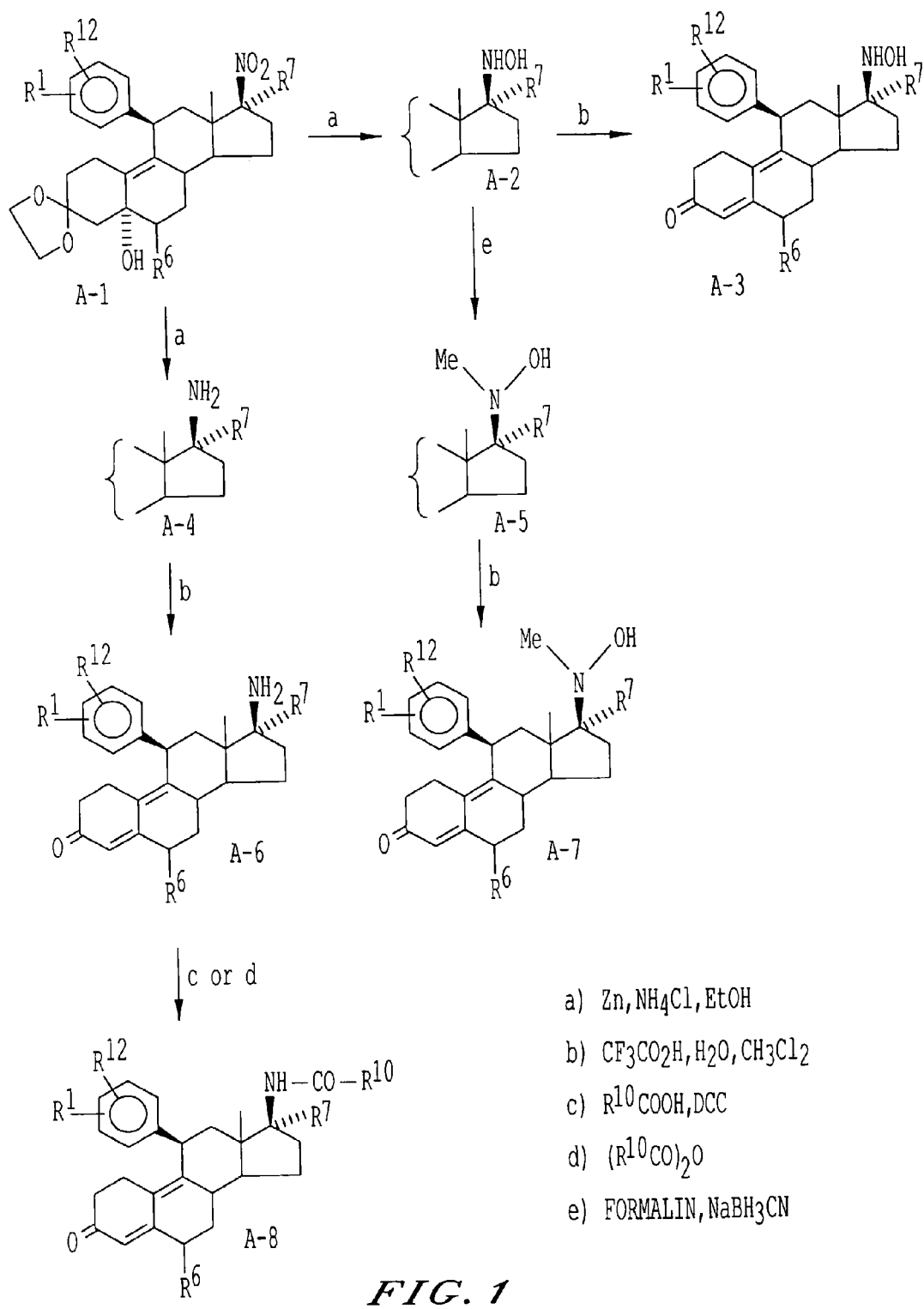
FIG. 1 depicts a reaction scheme to prepare amine and hydroxylamine compounds according to the present invention.

The above-identified compounds of formula I and II specifically include compounds which are susbsitituted on the A ring at the 3-position with two hydrogen atoms. These compounds are believed to undergo oxidation in vivo to the corresponding carbonyl compound.

Within the scope of the present invention, the term heteroatom means oxygen, nitrogen, sulfur, silicon or boron. Halogen means fluorine, chlorine, bromine or iodine and halo means fluoro, chloro, bromo or iodo. Aralkyl, aralkenyl, or aralkynyl means a $C_1$–$C_4$ alkyl, $C_2$–$C_4$ alkenyl or $C_2$–$C_4$ alkynyl group bearing an aryl substituent. Lower alkyl means a $C_1$–$C_6$ alkyl group. Heteroaryl means a unit of 5 to 12 non-hydrogen atoms consisting of one or more cyclic structures that may be fused or linked together, which contain 1 to 5 heteroatoms and which are generally accepted by those skilled in the art as having aromatic electronic character.

Heteroaralkyl, heteroaralkenyl, or heteroaralkynyl means a $C_1$–$C_4$ alkyl, $C_2$–$C_4$ alkenyl or $C_2$–$C_4$ alkynyl group bearing a heteroaryl substituent.

"Optionally substituted" means unsubstituted or substituted with one or more heteroatom(s) and/or halogens and/or alkyl groups of 1 to 4 carbon atoms and/or alkenyl and/or alkynyl groups of 2 to 4 carbon atoms and/or cycloalkyl groups of 3 to 7 carbon atoms and/or aryl groups of 6 to 12 carbon atoms and/or heteroaryl groups, and in which the alkyl, alkenyl, alkynyl, cycloalkyl, aryl or heteroaryl group may be further substituted with one or more heteroatoms and/or halogens. Substitution may occur directly on $CH_2$ groups of cyclic amine heterocycles. Where their valency permits, heteroatoms may be substituted either within the carbon chain or by attachment to it by single or double bonds. For example, —$CH_2CH_2C(=O)H$, —$CH_2(C=O)$$CH_3$, —$CH_2CH_2OCH_3$, —$CH_2CH_2CH_2OH$, $CH_3CH_2CH_2O$—, $CH_2CH_2C(=O)NH_2$, $CH_3CH_2C(=O)NH$—, —$CH_2CH_2COOCH_3$, $CH_3CH_2COO$—, and $CF_3CC$— all fall within this definition.

In all cases where valency and steric considerations permit, alkyl, alkenyl, alkynyl and cycloalkyl groups may contain additional double or triple bonds and/or branched chains.

The group $R^6$ at $C_6$ as it appears in structures I and II may be in either the α or β position. In a preferred embodiment, the group $R^6$ is located in the α-position.

In another embodiment, the $C_{11}β$-aryl group may be replaced with a pyridine group substituted with groups $R^1$ and $R^{12}$ as previously described.

In a preferred embodiment, the steroid having structure I is substituted as follows:

wherein $R^1$-Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl, 1-methylindol-5-yl or 1-methyl-2,3-dihydroindol-5-yl or $R^1$-Ph is the N-oxide of 4-(N,N-dimethyl)phenyl, 4-(N-piperidino)phenyl, 4-(N-pyrrolidino)phenyl, 4-(N-morpholino)phenyl;

X is O, NOH, or $NOCH_3$;

$R^6$ is H, $CH_3$, F or Cl;

$R^7$ is H, methyl, ethynyl, 1-propynyl, 3-propynyl, 3-hydroxypropyl, 3-hydroxy-1-propenyl (E- or Z-), 3,3,3-trifluropropyn-1-yl, 3-hydroxypropyn-1-yl, $(CH_2)_2COOCH_3$, $(CH_2)_2COOC_2H_5$, $(CH_2)_2COCH_3$, $CC$—$C_6H_5$, $CH_2C_6H_5$, CN, or $COOCH_3$;

$R^8$ is H, $CH_3$, or $CH_2C_6H_5$; and $R^9$ is H, OH, $OCH_3$, CHO, $CH_3CO$, $C_6H_5CO$ or $C_6H_5CH_2CO$.

In a preferred embodiment, the compound of structure II is substituted wherein, $R^1$-Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl, 1-methylindol-5-yl or 1-methyl-2,3-dihydroindol-5-yl);

X is O, NOH, or $NOCH_3$;

$R^6$ is H, $CH_3$, F or Cl;

$R^9$ is H, OH, CHO, $CH_3CO$, $C_6H_5CO$ or $C_6H_5CH_2CO$;

$R^{13}$ and $R^{14}$ are O, (H, H), (H, $CH_3$) or ($CH_3CH_3$); and $R^{15}$ and $R^{16}$ (H, H) or combine to form ($=CH_2$).

In a preferred embodiment the spirocyclic amino group at $C_{17}$ of the compound of structure II is such that the amine nitrogen is situated on the β-face of the compound, syn with the $C_{11}$ aryl group.

The compound of structure I, may also bear a nitrone functional group, when s is 0, $R^8$ is $O^-$ and $R^9$ is an alkene. In this case the nitrogen at the 17 position bears a positive charge.

Specific non-limiting examples include the compounds: 11β-(4-(N,N-dimethylamino)phenyl)-17β-(N-hydroxylamino)-17α-(1-propynyl)-estra-4,9-dien-3-one; 11β-(4-(N-piperidino)phenyl)-17β-(N-hydroxylamino)-17α-(1-propynyl)-estra-4,9-dien-3-one; 11β-(4-(N,N-dimethylamino)phenyl)-17β-(N-hydroxy-N-methylamino)-17α-(1-propynyl)estra-4,9-dien-3-one; 11β-(4-(N-piperidino)phenyl)-17β-(N-hydroxy-N-methylamino)-17α-(1-propynyl)estra-4,9-dien-3-one; 17β-amino-11β-(4-(N,N-dimethylamino)phenyl)-17α-(1-propynyl)estra-4,9-dien-3-one; 17β-amino-11-(4-(N-piperidino)phenyl)-17α-(1-propynyl)estra-4,9-dien-3-one; 17β-(N-acetamido)-11β-(4-(N,N-dimethylamino)phenyl)-17α-(1-propynyl)estra-4,9-dien-3-one; 17β-(N-acetamido)-11β-(4-(N-piperidino)phenyl)-17α-(1-propynyl)estra-4,9-dien-3-one; 11β-(4-(N,N-dimethylamino)phenyl)-17β-(N-formamido)-17α-(1-propynyl)estra-4,9-dien-3-one, and its N-oxide; 17β-(N-formamido)-11β-(4-(N-piperidino)phenyl)-17α-(1-propynyl)estra-4,9- dien-3-one and its N-oxide; 11β-(4-(N,N-dimethylamino)phenyl)-17β-(N-hydroxylamino)-17α-(3-hydroxypropyl)-estra-4,9-dien-3-one; 11β-(4-(N-piperidino)phenyl)-17β-(N-hydroxylamino)-17α-(3-hydroxypropyl)-estra-4,9-dien-3-one; 11β-(4-(N,N-dimethylamino)phenyl)-17β-(N-hydroxy-N-methylamino)-17α-(3-hydroxypropyl)estra-4,9-dien-3-one; 11β-(4-(N-piperidino)phenyl)-17β-(N-hydroxy-N-methylamino)-17α-(3-hydroxypropyl)estra-4,9-dien-3-one; 17β-amino-11β-(4-(N,N-dimethylamino)phenyl)-17α-(3-hydroxypropyl)estra-4,9-dien-3-one; 17β-amino-17α-(3-hydroxypropyl)-11β-(4-(N-piperidino)phenyl)estra-4,9-dien-3-one; 17β-(N-acetamido)-11β-(4-(N,N-dimethylamino)phenyl)-17α-(3-hydroxypropyl)estra-4,9-dien-3-one; 17β-(N-acetamido)-17α-(3-hydroxypropyl)-11β-(4-(N-piperidino)phenyl)estra-4,9-dien-3-one; 11β-(4-(N,N-dimethylamino)phenyl)-17β-(N-formamido)-17α-(3-hydroxypropyl)estra-4,9-dien-3-one; 17β-(N-formamido)-17α-(3-hydroxypropyl)-11β-(4-(N-piperidino)phenyl)estra-4,9-dien-3-one; 11β-(4-(N,N-dimethylamino)phenyl)-17β-(N-formamido)-17α-(3-formyloxy-1-propyl)estra-4,9-dien-3-one; 17β-(N-formamido)-17α-(3-formyloxy-1-propyl)-11β-(4-(N-piperidino)phenyl estra-4,9-dien-3-one; 11β-(4-(N,N-dimethylamino)phenyl)-1'-hydroxy-5'-methyl-spiro[estra-4,9-dien-17β,2'-pyrrolidine]-3-one; 11β-(4-(N-piperidino)phenyl)-1'-hydroxy-5'-methyl-spiro[estra-4,9-dien-17β,2'-pyrrolidine]-3-one; 11β-(4-(N,N-dimethylamino)phenyl)-1'-hydroxy-spiro[estra-4,9-dien-17β,2'-pyrrolidine]-3-one; 11β-(4-(N-piperidino)phenyl)-1'-hydroxy-spiro[estra-4,9-dien-17β,2'-pyrrolidine]-3-one; 11β-(4-(N,N-dimethylamino)phenyl)-5'-methyl-spiro[estra-4,9-dien-17β,2'-pyrrolidine]-3-one; 11β-(4-(N-piperidino)phenyl)-5'-methyl-spiro[estra-4,9-dien-17β,2'-pyrrolidine]-3-one; 11β-(4-(N,N-dimethylamino)phenyl)-spiro[estra-4,9-dien-17β,2'-pyrrolidine]-3-one; 11β-(4-(N-piperidino)phenyl)-spiro[estra-4,9-dien-17β,2'-pyrrolidine]-3-one; 11β-(4-(N,N-dimethylamino)phenyl)-5'-oxo-spiro[estra-4,9-dien-17β,2'-pyrrolidine]-3-one; 11β-(4-(N-piperidino)phenyl)-5'-oxo-spiro[estra-4,9-dien-17β,2'-pyrrolidine]-3-one; 11β-(4-(N,N-dimethylamino)phenyl)-1'-formyl-spiro[estra-4,9-dien-17β,2'-pyrrolidine]-3-one and 11β-(4-(N-piperidino)phenyl)-1'-formyl-spiro[estra-4,9-dien-17β,2'-pyrrolidine]-3-one.

Those compounds of the present invention which bear an amino group may also comprise a salt formed with the amine. Suitable pharmaceutically acceptable salts are known to those of ordinary skill in the art and comprise carboxylates, sulfates, phosphates and halides.

The amino and hydroxylamino compounds of the present invention may be prepared from an intermediate hydroxy nitro compound of structure (III)

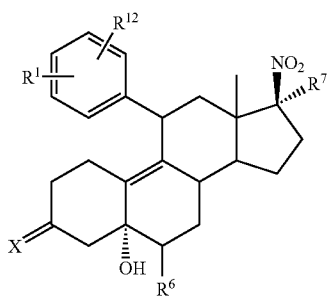

(III)

wherein
$R^1$ is $(R^2R^3N(O)_r)$—, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ aylkynyl, any of which may be optionally substituted; or

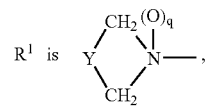

where q is 0 or 1, Y is —$(CH_2)_m$— where m is an integer of 0 to 5, or Y is —$(CH_2)_n$-Z-$(CH_2)_p$— where n is an integer of 0 to 2, p is an integer of 0 to 2, and Z is a heteroatom (optionally substituted) and where any of the $CH_2$ groups may be optionally substituted; or $R^1$ is N-imidazolyl-N-pyrrolyl-, H, halo-, HO—, $CF_3SO_2O$—, $C_{1-6}$ alkyl-O—, $C_{1-6}$ (alkyl-S—, $C_{1-6}$ alkyl-S(O)—, $C_{1-6}$ alkyl-S($O_2$)—, $C_{1-6}$ alkyl-CO—, $C_{1-6}$ alkyl-CH(OH)—, NC—, HCC—, $C_6H_5CC$—, 2'-furyl, 3'-furyl, 2'-thiophenyl, 3'-thiophenyl, 2'-pyridyl, 3'-pyridyl, 4'-pyridyl, 2'-thiazolyl, 2'-N-methylimidazolyl, 5'-pyrimidinyl, $C_6H_5$—, $H_2C$=CH—, $C_{1-6}$ alkyl, or MeC(=$CH_2$)—;

$R^{12}$ is H or halo; or $R^1$ and $R^{12}$ combine to form a ring

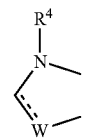

where W is $CH_2$, CH, NH, N, O, or S, and $R^4$ is H or $C_{1-6}$ alkyl;

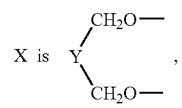

where Y is —$(CH_2)_m$— where m is an integer of 0 to 3, or Y is —$(CH_2)_n$-Z-$(CH_2)_p$— where n is an integer of 0 to 2, p is an integer of 0 to 2 and Z is a heteroatom (optionally substituted) or Z is a carbon atom substituted with one or two $C_{1-6}$ alkyl groups;

$R^6$ is H, $C_{1-6}$ alkyl or halogen;

$R^7$ is H, $C_{1-6}$ alkyl, $C_{2-6}$ alkenyl, $C_{2-6}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl, any of which may be optionally substituted, CN, $COOR^{10}$ or $CONHR^{10}$, where $R^{10}$ is H, $C_{1-18}$ alkyl, $C_{2-18}$ alkenyl, $C_{2-18}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl, any of which may be optionally substituted, by reduction of the nitro group, followed by hydrolysis of the ketal and elimination of the hydroxyl group. Such a method may be performed by conventional methods known to those of ordinary skill in the art. For example the nitro group may be reduced to an amine or hydroxylamine by treatment with zinc and ammonium chloride. The product amine or hydroxylamine my be favored by adjustment of the ratio of zinc to nitro compound, with lower molar ratios of zinc (2–18) favoring hyydroxylamine formation and higher ratios (20–80) favoring amine formation. Compounds of structure III may be made by the method described in U.S. patent application entitled "17β-Nitro-11β-aryl Steroids and Their Derivatives having Agonist or Antagonist Hormonal Properties" by C. E. Cook, J. A. Kepler, R. S. Shetty, G. S Bartley and D. Lee, filed concurrently with this application, 09/086,674, the relevant portions of which are hereby incorporated by reference.

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, endometriosis, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of value in control of hormonal irregularities in the menstrual cycle and for synchronization of fertile periods in cattle.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics, estrogens and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. For the specific-treatment of endometriosis or fibroids an amount of 0.01 to 10 mg/kg of body weight, preferably from 0.1 to 3 mg/kg may be administered. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated the time and route of administration; the rate of excretion: other drugs which have previously been administered; and the severity of the particular disease undergoing therapy, as is well understood by those of skill in the art.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiproizestins*, Committee on Antiprogestins: Assessing the Science, Institute of Medicine, National Academy Press, 1993. They are also useful as intermediates for the synthesis of other steroids.

Having generally described this invention, a further understanding can be obtained by reference to certain general examples which are provided herein for purposes of illustration only and are not intended to be limiting unless otherwise specified.

Synthetic Procedures

Figure 2:
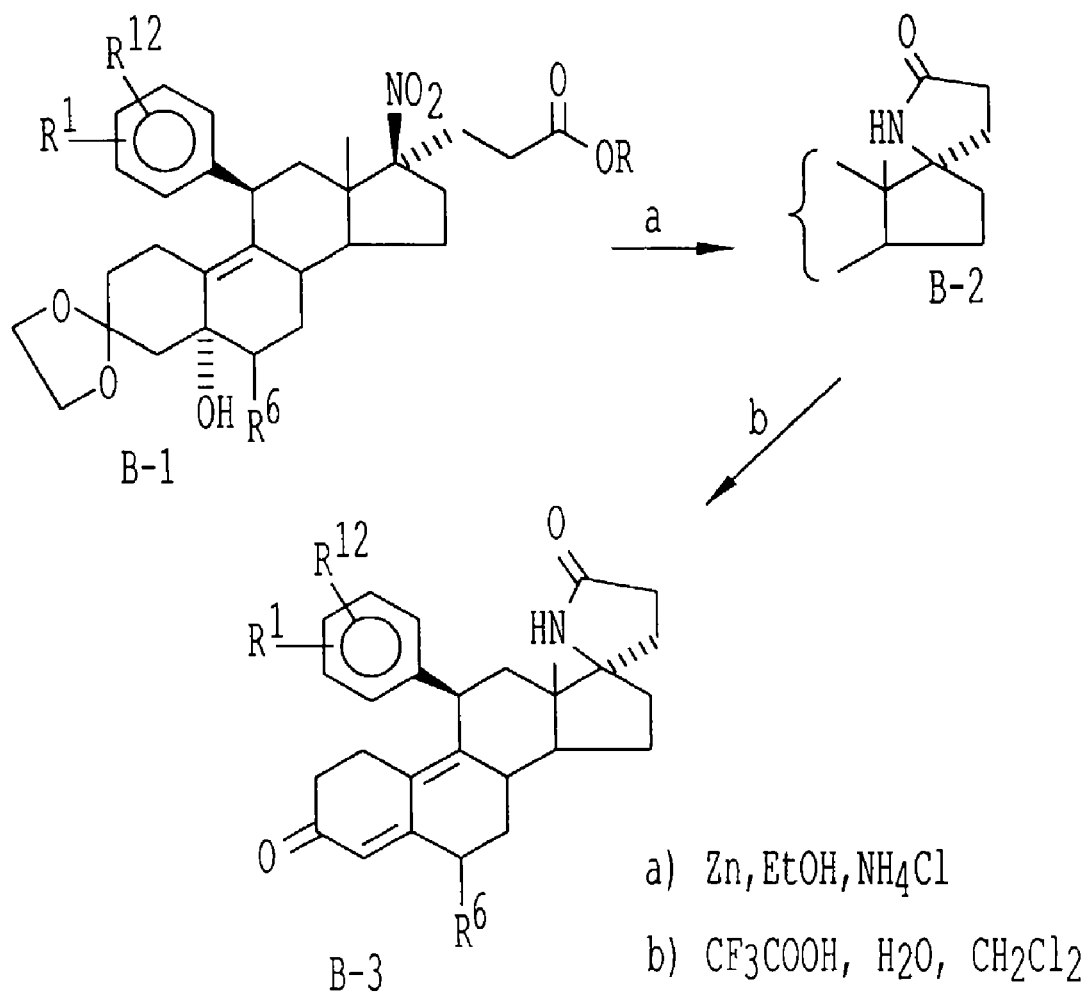
FIG. 2 depicts a reaction scheme to prepare cyclic amine compounds according to the present invention.
Figure 3:
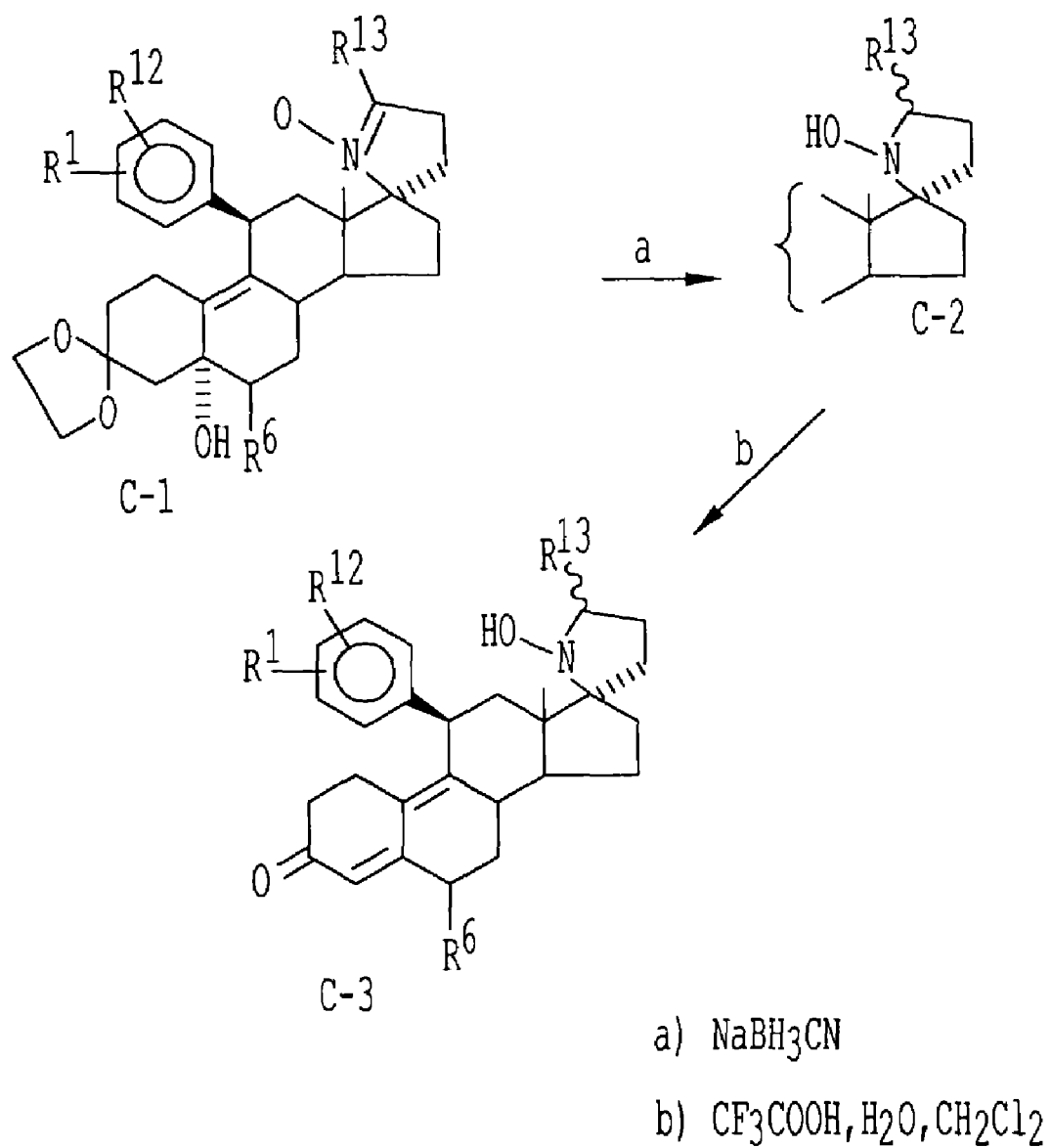
FIG. 3 depicts a reaction scheme to prepare cyclic hydroxylamine compounds according to the present invention.

Compounds of this invention may be made according to procedures such as those outlined in FIGS. 1 to 3 beginning with 11β-aryl-3,3-[1,2-ethanediylbis(oxy)]-5α-hydroxy-17β-nitroestr-9-enes (e.g., compound A-1 of FIG. 1 or analogous compounds) or with 3',4'-dihydro- 11β-aryl-3,3-[1,2-ethanediylbis(oxy)]-1'-oxo-spiro[estr-9-en-17β,2'(2'H)-pyrole]-5α-ols (e.g., compound C-1 of FIG. 3 or analogous compounds). Compounds of the type A-1 or C-1 may be prepared according to the procedures given in U.S. patent application entitled "17β-Nitro-11β-aryl Steroids and Their Derivatives having Agonist or Antagonist Hormonal Properties" by C. E. Cook, J. A. Kepler, R. S. Shetty, G. S Bartley and D. Lee, filed concurrently with this application, 09/086, 674.

Thus for example, treatment of A-1 with excess zinc dust (preferably around 9 atom-equivalents) and ammonium chloride in ethanol/water solution at around room temperature leads in good yield to the 17β-N-hydroxylamino compound A-2, which upon treatment with aqueous acid (preferably trifluoroacetic acid in water and $CH_2Cl_2$) undergoes ketal hydrolysis and dehydration to the 4,9-dien-3-one A-3.

If the intermediate hydroxylamine A-2 is treated with formalin and NaBH$_3$CN, the nitrogen is methylated to form intermediate 17β-N-methyl-N-hydroxy compound A-5, which can be hydrolyzed and dehydrated in the same manner as A-2 to yield the dienone A-7.

If compound A-1 is treated with excess zinc dust (preferably around 60 atom-equivalents) and ammonium chloride in ethanol/water/tetrahydrofuran (THF) solution at elevated temperatures (preferably around 70° C.), reduction of the nitro group leads to the 17β-amines A-4. These compounds could be hydrolyzed and dehydrated as described above to yield the dienones A-6. The amino group of A-6 may be further derivatized, for example by conversion to amides by methods well known to those skilled in the art. For example treatment of A-6 with formic acid and N,N-dicyclohexyl-carbodiimide (DCC) leads to the formamido compounds, whereas treatment with acetic anhydride in pyridine results in the formation of acetamido compounds.

If R$^7$ of compound A-1 terminates in a carboxyl or carboxyl ester function and the chain length permits, then reduction of the nitro group can lead to cyclization to the amide. Thus if R$^7$ is CH$_2$CH$_2$COOEt (compound B-1) and excess zinc is used for the reduction at elevated temperature, the cyclic amide B-2 is formed. Acid hydrolysis and dehydration then leads to dienone B-3. If R$^7$ of compound A-1 contains a carbonyl group (ketone or aldehyde) at an appropriate position in the chain, then reduction under milder conditions leads to the spironitrones such as compound C-1, the preparation of which is described in U.S. patent application entitled "17β-Nitro-11β-aryl Steroids and Their Derivatives having Agonist or Antagonist Hormonal Properties" by C. E. Cook, J. A. Kepler, R. S. Shetty, G. S Bartley and D. Lee, filed concurrently with this application, 09/086, 674. Reduction of the nitrone with, for example, sodium borohydride results in the N-hydroxyspiropyrrolidines C-2, which may also be hydrolyzed and dehydrated to the dienones as described above.

Compounds such as B-2 and C-2 are versatile intermediates, which can be converted to a variety of novel compounds by methods known to those skilled in the art, including N- or O-alkylation and/or reduction by hydride reagents to yield for example, cyclic amines, which can be further modified, e.g., by N-alkylation or N-acylation. Thus can be obtained various spiropyrrolidines analogs of B-2, B-3, C-2 and C-3.

Having generally described this invention, a further understanding can be obtained by reference to certain specific examples which are provided herein for purposes of illustration only and are not intended to be limiting unless otherwise specified.

General Procedures. Unless otherwise stated, reagent-grade chemicals were obtained from commercial sources and were used without further purification. Ether and tetrahydrofuran (THF) were freshly distilled from sodium benzophenone ketyl pair under nitrogen. All moisture- and air-sensitive reactions and reagent transfers were carried out under dry nitrogen or argon. Thin layer chromatography (TLC) was performed on EM Science precoated silica gel 60 F-254 plates. Compounds were normally visualized by UV light (254 nm) or p-anisaldehyde spray. Preparative column chromatography employed EM Science silica gel, 60 Å (230–400 mesh). Solutions were concentrated by use of a rotary evaporator under water aspirator pressure at ambient temperature. Melting points were taken on a Mel-Temp II and are uncorrected. Unless otherwise noted, $^1$H NMR spectra were obtained at 250 MHz on a Bruker AC 250 spectrometer in CDCl$_3$ as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

EXAMPLE 1

Synthesis of 11β-[4-(N,N-Dimethylamino)phenyl]-17β-(N-hydroxylamino)-17α-(1-propynyl)estra-4,9-dien-3-one [A-3 (R$^1$=4-Me$_2$N—, R$^7$=CH$_3$CC—, R$^6$=R$^{12}$=H)]

11β-[4-(N,N-Dimethylamino)phenyl]-3,3-[1,2-ethanediylbis(oxy)]-5α-hydroxy-17β-(N-hydroxylamino)-17α-(1-propynyl)estr-9-ene [A-2 (R$^1$=4-Me$_2$N—, R$^7$=CH$_3$CC—, R$^6$=R$^{12}$=H)]. To a homogeneous solution of 6.34 g (12.2 mmol) of nitropropyne A-1 (R$^1$=4-Me$_2$N—, R$^7$=CH$_3$CC—, R$^6$=R$^{12}$=H) and 1.37 g (25.6 mmol) of NH$_4$Cl in 160 mL of THF, 80 mL of EtOH, and 80 mL of water at room temperature was added 7.17 g (110 mmol) of zinc dust (–325 mesh). After stirring for 1.5 h, the mixture was filtered through a pad of Celite with the aid of EtOAc. The filtrate was washed three times with brine, dried over Na$_2$SO$_4$, filtered, and the solvent was removed under reduced pressure to afford a white amorphous solid (6.42 g). Chromatography on silica gel (70% EtOAc in hexanes) afforded hydroxylamine A-2 (R$^1$=4-Me$_2$N—, R$^7$=CH$_3$CC—, R$^6$=R$^{12}$=H) (3.60 g, 60% yield). $^1$H NMR (250 MHz, CDCl$_3$) δ 7.05 (2H, d, J=8.6 Hz), 6.64 (2H, d, J=8.8 Hz), 5.02 (1H, br s), 4.43 (1H, s), 4.21 (1H, d, J=6.2 Hz), 4.02–3.92 (4H, m), 2.90 (6H, s), 1.91 (1H, s), 0.48 (3H, s).

11β-[4-(N,N-Dimethylamino)phenyl]-17β-(N-hydroxylamino)-17α-(1-propynyl)estra-4,9-dien-3-one [A-3 (R$^1$=4-Me$_2$N—, R$^7$=CH$_3$CC—, R$^6$=R$^{12}$=H)]. A mixture of 3.60 g (7.11 mmol) of hydroxyketal A-2 (R$^1$=4-Me$_2$N—, R$^7$=CH$_3$CC—, R$^6$=R$^{12}$=H) in 316 mL of CH$_2$Cl$_2$ and 6.3 mL of water was stirred vigorously while cooling in an ice-water bath for 1.5 h. To the rapidly stirred dispersion was added dropwise 8.80 mL (114 mmol) of trifluoroacetic acid. After stirring vigorously for 3 h, excess saturated aqueous NaHCO$_3$ solution was added slowly and the mixture was allowed to stir at room temperature for 20 min. The aqueous layer was separated and extracted three times with EtOAc. The combined organic solutions were washed twice with brine, dried over Na$_2$SO$_4$, filtered, and the solvent was removed under reduced pressure to give a yellow solid (3.11 g). The material was chromatographed on silica gel (70% EtOAc in hexanes). Combination of the resulting fractions of >97% purity (as determined by HPLC analysis) afforded hydroxylamine dienone A-3 (R$^1$=4-Me$_2$N—, R$^7$=CH$_3$CC—, R$^6$=R$^{12}$=H) (2.37 g, 75% yield) [mp 100–117° C. (amorphous)]. The sample could be dried in vacuo at 92° C. for 14 h to provide solvent-free product with no loss of purity. $^1$H NMR (250 MHz, CDCl$_3$) δ 7.01 (2H, d, J=8.5 Hz), 6.65 (2H, d, J=8.9 Hz), 5.75 (1H, s), 5.16 (1H, br s), 4.65 (1H, s), 4.31 (1H, br s), 2.91 (6H, s), 1.94 (3H, s), 0.55 (3H, s). Anal. Calcd. for C$_{29}$H$_{36}$N$_2$O$_2$.0.5H$_2$O: C, 76.79; H, 8.22; N, 6.18. Found: C, 76.82; H, 8.29; N, 6.12. MS m/z (rel inten) 444 (M$^+$, 12), 428 (12), 411 (23), 134 (51), 121 (100).

EXAMPLE 2

Synthesis of 11β-[4-(N,N-Dimethylamino)phenyl]-17β-(N-hydroxy-N-methylamino)-17α-(1-propynyl)estra-4,9-dien-3-one [A-7 ($R^1$=4-$Me_2$N—, $R^7$=$CH_3$CC—, $R^6$=$R^{12}$=H)]

11β-[4-(N,N-Dimethylamino)phenyl]-3,3-[1,2-ethanediylbis(oxy)]-5α-hydroxy-17β-(N-hydroxy-N-methylamino)-17α-(1-propynyl)estr-9-ene [A-5 ($R^1$=4-$Me_2$N—, $R^7$=$CH_3$CC—, $R^6$=$R^{12}$=H)]. To a solution of 232 mg (0.458 mmol) of hydroxylamine A-2 ($R^1$=4-$Me_2$N—, $R^7$=$CH_3$CC—, $R^6$=$R^{12}$=H) in 4.6 mL of $CH_3$CN at room temperature was added 0.19 mL (2.3 mmol) of formalin, then 49 mg (0.733 mmol) of $NaBH_3$CN. After 45 min, the white precipitate-containing basic reaction mixture [pH 8–9 (as determined by pre-$H_2$O-wetted pH paper)] was brought to pH 7 by the addition of three small portions (ca. 1 drop total) of glacial acetic acid, thus causing homogeneity. After 1.5 h, the solution was measured to be pH 8, then another small amount (ca. 0.25 drop) of glacial acetic acid was added, then 40 min later, saturated aqueous $NaHCO_3$ and EtOAc were added. The aqueous layer was separated and extracted three times with EtOAc. The combined organic solutions were washed twice with brine, dried over $Na_2SO_4$, filtered, and the solvent was removed under reduced pressure. The resulting white foam was purified by chromatography on silica gel (60% EtOAc in hexanes) to afford N-methylhydroxylamine A-5 ($R^1$=4-$Me_2$N—, $R^7$=$CH_3$CC—, $R^6$=$R^{12}$=H) (74 mg, 31% yield). $^1$H NMR (250 MHz, $CDCl_3$) δ 7.04 (2H, d, J=8.7 Hz), 6.63 (2H, d, J=8.7 Hz), 4.42 (1H, s), 4.16 (1H, br s), 4.02–3.92 (4H, m), 2.89 (6H, s), 2.54 (3H, s), 0.51 (3H, s).

11β-[4-(N,N-Dimethylamino)phenyl]-17β-(N-hydroxy-N-methylamino)-17α-(1-propynyl)estra-4,9-dien-3-one [A-7 ($R^1$=4-$Me_2$N—, $R^7$=$CH_3$CC—, $R^6$=$R^{12}$=H)]. To a vigorously stirred mixture of 122 mg (234 mmol) of N-methylhydroxylamine ketal A-5 ($R^1$=4-$Me_2$N—, $R^7$=$CH_3$CC—, $R^6$=$R^{12}$=H) in 10.2 mL of $CH_2Cl_2$ and 0.5 mL of $CDCl_3$ and 0.21 mL of water at 0° C. was added dropwise 0.29 mL (3.76 mmol) of trifluoroacetic acid. After stirring vigorously for 5.5 h at 0° C., saturated aqueous $NaHCO_3$ was added and the mixture was stirred for 30 min, then diluted with EtOAc. The aqueous layer was separated and extracted three times with EtOAc. The combined organic solutions were washed twice with brine, dried over $Na_2SO_4$, filtered, and the solvent was removed under reduced pressure, giving a yellow foam (118 mg). The product was purified by flash chromatography on silica gel (80% EtOAc in hexanes), then by flash chromatography on silica gel (1.1:30:68.9, MeOH-THF-hexanes), then by medium pressure chromatography on silica gel (hexanes, then 30% THF in hexanes), and then by reverse-phase preparative HPLC (20% $H_2$O in MeOH) to afford methylhydroxylamine dienone A-7 ($R^1$=4-$Me_2$N—, $R^7$=$CH_3$CC—, $R^6$=$R^{12}$=H) (29.0 mg, 27% yield) in >97% purity, as determined by HPLC analysis. $^1$H NMR (250 MHz, $CDCl_3$) δ 7.00 (2H, d, J=8.5 Hz), 6.65 (2H, d, J=8.8 Hz), 5.75 (1H, s), 4.28 (1H, d, J=6.4 Hz), 2.91 (6H, s), 2.57 (3H, s), 1.98 (3H, s), 0.58 (3H, s). Anal. Calcd. for $C_{30}H_{38}N_2O_2 \cdot 0.75H_2O$: C, 76.32; H, 8.43; N, 5.93. Found: C, 76.62; H, 8.17; N, 5.87. MS m/z (rel inten) 458 ($M^+$, 13), 441 (32), 411 (21), 320 (24), 278 (23), 225 (23), 121 (100).

EXAMPLE 3

Synthesis of 17β-Amino-11β-[4-(N,N-dimethylamino)phenyl]-17α-(1-propynyl)estra-4,9-dien-3-one [A-6 ($R^1$=4-$Me_2$N—, $R^7$=$CH_3$CC—, $R^6$=$R^{12}$=H)]

17β-Amino-11β-[4-(N,N-dimethylamino)phenyl]-3,3-[1,2-ethanediylbis(oxy)]-5α-hydroxy-17α-(1-propynyl)estr-9-ene [A-4 ($R^1$=4-$Me_2$N—, $R^7$=$CH_3$CC—, $R^6$=$R^{12}$=H)]. To a homogeneous solution of 5.00 g (9.60 mmol) of nitropropyne A-1 ($R^1$=4-$Me_2$N—, $R^7$=$CH_3$CC—, $R^6$=$R^{12}$=H) and 10.3 g (192 mmol) of $NH_4$Cl in 100 mL of THF, 50 mL of EtOH, and 50 mL of water at 70° C. was added 37.7 g (576 mmol) of zinc dust (−325 mesh). After stirring efficiently for 7.5 h, the mixture was allowed to cool to room temperature and was suction filtered through a pad of Celite with the aid of EtOAc. The filtrate was washed three times with brine, dried over $Na_2SO_4$, filtered, and the solvent was removed under reduced pressure to give a yellow foam (4.95 g). Chromatography on silica gel (20% MeOH in EtOAc) provided aminopropyne A-4 ($R^1$=4-$Me_2$N—, $R^7$=$CH_3$CC—, $R^6$=$R^{12}$=H) (3.48 g, 74% yield). $^1$H NMR (250 MHz, $CDCl_3$) δ 7.06 (2H, d, J=8.5 Hz), 6.64 (2H, d, J=8.8 Hz), 4.42 (1H, br s), 4.25 (1H, d, J=6.9 Hz), 4.03–3.90 (4H, m), 2.91 (6H, s), 1.84 (3H, s) 0.40 (3H, s).

17β-Amino-11β-[4-(N,N-dimethylamino)phenyl]-17α-(1-propynyl)estra-4,9-dien-3-one [A-6 ($R^1$=4-$Me_2$N—, $R^7$=$CH_3$CC—, $R^6$=$R^{12}$=H)]. A mixture of 265 mg (0.540 mmol) of aminopropyne ketal A-4 ($R^1$=4-$Me_2$N—, $R^7$=$CH_3$CC—, $R^6$=$R^{12}$=H) in 24 mL of $CH_2Cl_2$ and 0.48 mL of water was stirred vigorously in an ice-water bath for 1.5 h. To the rapidly stirred dispersion was added dropwise 0.67 mL (8.69 mmol) of trifluoroacetic acid. After stirring vigorously for 4.5 h, excess saturated aqueous $NaHCO_3$ solution was added slowly, then the mixture was stirred for 30 min at room temperature. The aqueous layer was separated and extracted three times with brine, dried over $Na_2SO_4$, filtered, and the solvent was removed under reduced pressure to give a yellow oil (258 mg). The material prepared in this fashion was highly pure by $^1$H NMR analysis, and in analogous experiments could be used in subsequent transformations without further purification. A sample of >97% purity (as determined by HPLC analysis) was prepared by chromatography on silica gel (12% MeOH in EtOAc), then by chromatography on silica gel (10% MeOH in EtOAc), then by chromatography on $Et_3$N-deactivated silica gel (50% EtOAc in hexanes), and then chromatographed by reverse-phase preparative HPLC [30% $H_2$O in MeOH containing $Et_3$N (50 mM)] to afford dienone A-6 ($R^1$=4-$Me_2$N—, $R^7$=$CH_3$CC—, $R^6$=$R^{12}$=H) (44.6 mg, 19% yield). $^1$H NMR (250 MHz, $CDCl_3$) δ 7.03 (2H, d, J=8.7 Hz), 6.66 (2H, d, J=8.9 Hz), 5.76 (1H, s), 4.36 (1H, d, J=7.3 Hz), 2.92 (6H, s), 1.84 (3H, s), 0.48 (1H, s). Anal. Calcd. for $C_{29}H_{36}N_2O$: C, 81.27; H, 8.47; N, 6.54. Found: C, 81.21; H, 8.50; N, 6.49. MS m/z (rel inten) 428 ($M^+$, 61), 411(97), 278 (33), 134 (100).

EXAMPLE 4

Synthesis of 17β-(N-Acetamido)-11β-[4-(N,N-dimethylamino)phenyl]-17α-(1-propynyl)estra-4,9-dien-3-one [A-8 ($R^1$=4-$Me_2N$—, $R^7$=$CH_3CC$—, $R^{10}$=$CH_3$, $R^6$=$R^{12}$=H)]

To a solution of 72 mg (0.168 mmol) of aminodienone A-6 ($R^1$=4-$Me_2N$—, $R^7$=$CH_3CC$—, $R^6$=$R^{12}$=H) in 1.6 mL of pyridine at 0° C. was added 18.0 mL (185 mmol) of $Ac_2O$. After 2.5 h, one drop of $Ac_2O$ was added, and after 30 min, the solution was partially concentrated under a slow stream of nitrogen. The resulting yellow-brown oil was combined with 19 mg of previously obtained product, then chromatographed on silica gel (90% EtOAc in hexanes) to give dienone acetamide A-8 ($R^1$=4-$Me_2N$—, $R^7$=$CH_3CC$—, $R^{10}$=$CH_3$, $R^6$=$R^{12}$=H) (64.8 mg) as a solid. Three subsequent reverse-phase MPLC purifications (80:20, MeOH—$H_2O$, 75:25, MeOH—$H_2O$, and 77.5:22.5, MeOH—$H_2O$) afforded dienone A-8 ($R^1$=4-$Me_2N$—, $R^{10}$=$CH_3$, $R^7$=$CH_3CC$—, $R^6$=$R^{12}$=H) (37.7 mg, 38% yield [adjusted]) in >97% purity as determined by HPLC analysis. $^1$H NMR (250 MHz, $CDCl_3$) δ 7.03 (2H, d, J=8.6 Hz), 6.70 (2H, d, J=8.8 Hz), 5.67 (1H, s), 5.55 (1H, br s), 4.36 (1H, d, J=6.2 Hz), 2.92 (6H, s), 1.93 (3H, s), 1.87 (3H, s), 0.49 (3H, s). Anal. Calcd. for $C_{31}H_{38}N_2O_2\cdot 0.5H_2O$: C, 77.63; H, 8.20; N, 5.84. Found: C, 77.30; H, 8.20; N, 5.77. MS m/z (rel inten) 470 ($M^+$, 100), 411 (9), 280 (44), 121 (41).

EXAMPLE 5

11β-[4-(N,N-Dimethylamino)phenyl]-17β-(N-formamido)-17α-(1-propynyl)estra-4,9-dien-3-one [A-8 ($R^1$=4-$Me_2N$—, $R^7$=$CH_3CC$—, $R^{10}$=$R^6$=$R^{12}$=H)]

To a solution of 2.11 g (10.2 mmol) of dicyclohexylcarbodiimide in 11 mL of $CHCl_3$ at room temperature was added 20.4 mL (20.4 mmol) of 1.00 M formic acid in $CHCl_3$, causing a white precipitate. After 45 min, the mixture was added to a solution of 2.19 g (5.11 mmol) of aminopropyne A-6 ($R^1$=4-$Me_2N$—, $R^7$=$CH_3CC$—, $R^6$=$R^{12}$=H) and 2.47 mL (30.7 mmol) of pyridine in 22 mL of $CHCl_3$. After 20 min, 66 mL of ether was added and the resulting mixture was filtered through a pad of Celite, rinsing six times with 10 mL of ether. The filtrate was concentrated under reduced pressure, then diluted with 22 mL of EtOAc and stirred for 10 min. The resulting mixture was filtered through a pad of Celite, rinsing eight times with 3 mL of EtOAc. The filtrate was concentrated under reduced pressure. The residue was iteratively diluted three times with 11 mL of toluene and concentrated under reduced pressure by rotary evaporation. After further solvent removal in vacuo, the light green residue was free of pyridine by $^1$H NMR analysis and was chromatographed on silica gel (75% EtOAc in hexanes) to afford formamide A-8 ($R^1$=4-$Me_2N$—, $R^7$=$CH_3CC$—, $R^{10}$=$R^6$=$R^{12}$=H) (1.56 g, 67% yield) [mp 128–142° C. (amorphous)]. The product was determined to be >97% pure by HPLC analysis, and could be heated in vacuo at 90° C. for 16 h to provide solvent-free product, with conservation of >97% purity by HPLC analysis. This compound existed as a mixture of equilibrating forms (observable by $^1$HNMR). $^1$H NMR (250 MHz, $CDCl_3$, integration adjusted for ratio of major and minor forms) δ 8.52 (1H, d, J=11.7 Hz), 6.98 (2H, d, J=8.6 Hz), 6.64 (2H, d, J=8.8 Hz), 6.21 (1H, d, J=11.8 Hz), 5.77 (1H, s), 4.37 (1H, d, J=6.7 Hz), 2.91 (6H, s), 1.90 (3H, s), 0.47 (3H, s) minor form: 8.08 (1H, s), 7.04 (shoulder), 5.68 (1H, s), 1.88 (3H, s), 0.50 (shoulder). Anal. Calcd. for $C_{30}H_{36}N_2O_2\cdot 1.25H_2O$: C, 75.20; H, 8.10; N, 5.85. Found: C, 75.17; H, 7.56; N, 5.80. MS m/z (rel inten) 456 ($M^+$, 94), 280 (44), 134 (51), 121 (100).

EXAMPLE 6

Synthesis of 17β-Amino-17α-(3-hydroxypropyl)-11β-[4-(N-piperidino)phenyl]estra-4,9-dien-3-one [A-6 ($R^1$=4-(N-piperidino)-, $R^7$=—$(CH_2)_3OH$, $R^6$=$R^{12}$=H)]

3,3-[1,2-Ethanediylbis(oxy)]-5α,10α-oxidoestr-9(11)-en-17-one. To a solution of 32.0 g (102 mmol) of 3,3-[1,2-ethanediylbis(oxy)]estra-5(10),9(11)-dien-17-one in 192 mL of $CH_2Cl_2$ at 0° C. was added 7.04 mL (50.9 mmol) of hexafluoroacetone trihydrate (Lancaster Synthesis, Inc.) followed by 2.46 g (17.3 mmol) of $Na_2HPO_4$, and then 8.64 mL (153 mmol) of 50% $H_2O_2$ was added dropwise to the efficiently stirred mixture (overhead mechanical stirring). Efficient stirring was continued for 18 h, during which time the temperature was allowed to gradually rise to room temperature, then 192 mL of saturated aqueous $Na_2S_2O_3$ was added. After stirring for 20 min, the mixture was combined with another (32.0 g) batch which had been prepared identically up to this point in parallel. The aqueous layer (bottom) was separated and extracted three times with 80 mL of EtOAc. The combined organic solutions were diluted with 240 mL of EtOAc and washed twice with 80 mL of saturated aqueous $NaHCO_3$ solution, twice with 80 mL of brine, dried over $MgSO_4$, filtered, and the solvent was removed under reduced pressure. The yellow solid (76.1 g) was triturated with 320 mL of diethyl ether with magnetic stirring for 12 h in a closed flask. The resulting white slurry was combined with three other batches (3×32.0 g) which had been prepared identically (and proportionally) to this point, in parallel, then suction filtered through a coarse-porosity sintered glass funnel, rinsing three times with 40 mL of diethyl ether, then allowed to suck dry for 1.5 h. The resulting white filter cake was gently scraped into a fine white powder and dried in vacuo to afford the desired epoxide of high purity (89.5 g, 53% yield). $^1$H NMR (250 MHz, $CDCl_3$) δ 6.06 (1H, br s), 3.98–3.88 (4H, m), 2.52–2.44 (2H, m) 1.32–1.12 (1H, m), 0.88 (3H, s).

1-(4-Bromophenyl)piperidine. To a solution of 320 g (1.86 mmol, 1.00 eq) of 4-bromoaniline in 1.20 L of toluene at room temperature in a 5 L round bottomed flask equipped with an overhead mechanical stirrer was added 648 mL (3.72 mmol, 2.00 eq) of diisopropylethylamine then 253 mL (1.86 mmol, 1.00 eq) of 1,5-dibromopentane followed by rinsing with 200 mL of toluene. With a heating mantle, the efficiently stirred solution was heated to 100° C. to 115° C., as determined by a thermometer immersed in the reaction solution. After 10 h, high conversion to desired product was observed by TLC analysis. The resulting voluminous precipitate-containing brown mixture was allowed to cool to room temperature. The mixture was crushed with a spatula into a transferable slurry with the aid of 390 mL of toluene. The diisopropylethylamine hydrochloride solids were removed by suction filtration through a coarse porosity fritted funnel followed by rinsing the solids with toluene (3×320 mL). (Further toluene rinses of the resulting brown solids yielded only an insignificant amount of material.) Rotary evaporation under reduced pressure of the brown filtrate followed by further solvent removal in vacuo for 12 h at room temperature afforded a soft brown solid (398 g, 89% crude yield) which was crushed into small pieces. 20.0 g of this crude material was removed for experimental optimization, resulting in the following purification protocol.

To the remainder of the crude product (378 g) was added, in five 300 mL portions, 1.50 L of diethyl ether with efficient magnetic stirring. After 30 min. at room temperature, stirring was discontinued and the stir bar was removed. A dark insoluble fine solid was allowed to settle, and the brown solution was carefully decanted, rinsing the brown solids with diethyl ether (3×100 mL). To the combined brown ethereal solutions at room temperature was added 38.5 mL (406 mmol) of acetic anhydride. After stirring for 3 h at room temperature, 300 mL of aqueous 10% hydrochloric acid (i.e. 3.7% $HCl_{(aq)}$ was added at room temperature and the mixture was efficiently stirred for 5 min, during which time a small amount of a yellow precipitate formed. The ether layer was separated and extracted with aqueous 10% hydrochloric acid (5×300 mL). The combined acidic aqueous solutions were decanted to remove a small amount of a yellow solid and then back-extracted once with 150 mL of diethyl ether. The aqueous solution was basified to pH 10 with efficient stirring at room temperature by the slow addition of 235 mL of concentrated ammonium hydroxide over 20 min. To the resulting yellow/white precipitate-containing mixture was added 600 mL of diethyl ether with rapid stirring, thus completely dissolving the solids after ca. 10 min. The aqueous layer was separated and extracted with diethyl ether (2×150 mL). The combined ethereal solutions were washed with brine (2×150 mL), dried over $Na_2SO_4$, filtered, and the solvent was removed by rotary evaporation under reduced pressure. Further solvent removal in vacuo for 12 h afforded the highly pure product as an off-white solid [338 g, 80% yield (adjusted for the 20.0 g removal)]. $^1H$ NMR (250 MHz, $CDCl_3$) δ 7.29 (2H, d, J=9.1 Hz), 6.76 (2H, d, J=9.1 Hz), 3.11–3.07 (4H, m), 1.73–1.66 (4H, m), 1.59–1.51 (2H, m).

3,3-[1,2-Ethanediylbis(oxy)]-5α-hydroxy-11β-[4-(N-piperidino)phenyl]estr-9-en-17-one. A 3 L round-bottomed flask equipped with an overhead mechanical stirrer and charged with 9.67 g (398 mmol) of magnesium turnings was flame-dried under a stream of dry nitrogen. After cooling to room temperature, 333 mL of THF was added followed by a few crystals of iodine, thus imparting a light brown coloration. To the efficiently stirred mixture was added 40 mL of a solution of 91.9 g (383 mmol) of 1-(4-bromophenyl)piperidine in 333 mL of THF. After heating the mixture to reflux for ca. 5 min, the iodine color quickly faded to colorless, at which time the mixture was allowed to cool nearly to room temperature. The remainder of the bromide solution was added dropwise over a period of 1.5 h. The mixture was then cooled in an ice-water bath for 1.8 h, then 15.1 g (153 mmol) of finely powdered CuCl was added in one portion. After the mixture was stirred efficiently for 60 sec, a solution of 50.6 g (153 mmol) of 3,3-[1,2-ethanediyl-bis(oxy)]-5α,10α-oxidoestr-9(11)-en-17-one in 380 mL of THF was added (poured in) over 30 sec, causing the formation of a voluminous light yellow precipitate. After 10 min, 250 mL of saturated aqueous $NH_4Cl$ solution was slowly added, followed by 630 mL of EtOAc. After stirring for 30 min, the mixture was diluted and stirred with 300 mL of water. The aqueous layer was separated and extracted three times with 250 mL of EtOAc. The combined organic solutions were washed three times with 250 mL of brine, dried over $MgSO_4$, filtered, and the solvent was removed under reduced pressure. The resulting material (116 g) was combined with an analogously prepared batch of crude product (11.3 g) in 55 mL of $CH_2Cl_2$, then chromatogtaphed on silica gel (elution of piperidinophenyl reagent by-product with $CH_2Cl_2$, then elution of product with 60% EtOAc in hexanes) to afford the desired product, in which some fractions contained a minor amount of a bis-adduct in which Grignard reagent had undergone addition to the 17-carbonyl group. Thus, another chromatography of the concentrated contaminated fractions on silica gel (60% EtOAc in hexanes) with combination of the resulting pure fractions with the pure fractions from the first chromatographic separation afforded contaminant-free product (65.2 g, 79% adjusted yield). $^1H$ NMR (250 MHz, $CDCl_3$) δ 7.07 (2H, d, J=8.6 Hz), 6.83 (2H, d, J=8.7 Hz), 4.53 (1H, s), 4.30 (1H, d, J=6.8 Hz), 4.02–3.92 (4H, m), 3.13–3.08 (4H, m), 0.50 (3H, s).

3,3-[1,2-Ethanediylbis(oxy)]-5α-hydroxy-11β-[4-(N-piperidino)phenyl]estr-9-en-17-oxime.

To a solution of 65.1 g (132 mmol) of 3,3-[1,2-ethanediylbis(oxy)]-5α-hydroxy-11β-[4-(N-piperidino)phenyl]estr-9-en-17-one in 450 mL of anhydrous pyridine at room temperature under nitrogen was added 15.2 g (218 mmol) of hydroxylamine hydrochloride. After stirring for 19.5 h, 1.50 L of water and 475 mL of EtOAc were added. After stirring for 10 min, the aqueous layer was separated and extracted three times with 275 mL of EtOAc. The combined organic solutions were washed twice with 275 mL of brine, dried over $Na_2SO_4$, filtered, and the solvent was removed under reduced pressure. The resulting foam was iteratively rotary evaporated under reduced pressure three times with 275 mL of toluene at 40° C., during which time 4.93 g of analogously prepared material was combined. Further solvent was removed in vacuo, thus affording the desired oxime as a yellow foam (81.7 g) free of pyridine by $^1H$ NMR analysis. The material was carried on without further purification. $^1H$ NMR (250 MHz, $CDCl_3$) δ 8.37 (1H, br s), 7.08 (2H, d, J=9.0 Hz), 6.81 (2H, d, J=8.6 Hz), 4.37 (1H, s), 4.22 (1H, d, J=6.6 Hz), 4.08–3.89 (4H, m), 3.12–3.08 (4H, m), 0.54 (3H, s).

3,3-[1,2-Ethanediylbis(oxy)]-5α-hydroxy-11β-[4-(N-piperidino-N-oxide)phenyl]estr-9-en-17-oxime. To a solution of 81.7 g (148 mmol assumed) of 3,3-[1,2-ethanediylbis(oxy)]-5α-hydroxy-11β-[4-(N-piperidino)phenyl]estr-9-en-17-oxime in 290 mL of $CH_2Cl_2$ at 0° C. was added 10.3 mL (73.7 mmol) of hexafluoroacetone trihydrate. With vigorous stirring, 17.8 mL (310 mmol) of 50% $H_2O_2$ was added dropwise. The mixture was stirred vigorously for 14.5 h, during which time the mixture had gradually warmed to room temperature. Water (414 mL) and EtOAc (1.65 L) were added, and the resulting mixture was stirred well for 20 min. The organic layer was separated and extracted five times with 125 mL of water. The combined aqueous solutions were carried on to the next step without further manipulation. A small aliquot could be concentrated in vacuo for characterization: $^1H$ NMR (250 MHz, $CDCl_3$) δ 10.7 (1H, br s), 7.96 (2H, d, J=8.6 Hz), 7.36 (2H, d, J=8.6 Hz), 4.39–4.32 (1H, m), 4.05–3.97 (4H, m), 3.68–3.56 (2H, m), 3.44–3.39 (2H, s).

17-Bromo-3,3-[1,2-ethanediylbis(oxy)]-5α-hydroxy-17-nitro-11β-[4-(N-piperidino)-phenyl]estr-9-ene [A-1 ($R^1$=4-(N-piperidino)-, $R^7$=Br, $R^6$=$R^{12}$=H)]. To a solution of 65.9 g (369 mmol) of N-bromosuccinimide (NBS) in 375 mL of 1,4-dioxane at room temperature was added a solution of 37.0 g (369 mmol) of KHCO, in 375 mL of water. After 5 min, the above aqueous solution of 3,3-[1,2-ethanediylbis(oxy)]-5α-hydroxy-11β-[4-(N-piperidino-N-oxide)phenyl]estr-9-en-17-oxime at room temperature was diluted with 720 mL of 1,4-dioxane, then slowly added to the NBS—$KHCO_3$ solution at such a rate so as to avoid excessive gas evolution and foaming. After stirring the solution at room temperature for 16 h, 262 g (944 mmol) of FeSO$_4$.7H$_2$O was added, causing a voluminous brown precipitate, then 375 mL of EtOAc and 650 mL of water were added. After stirring efficiently for 30 min, the aqueous layer was separated and extracted four times with 300 mL of EtOAc. The combined organic solutions were washed twice with 300 mL of brine, dried over Na$_2$SO$_4$, filtered, and the solvent was removed under reduced pressure to afford A-1 (R$^1$=4-N-piperidino)-, R$^7$=Br, R$^6$=R$^{12}$=H) as a brown foam (69.3 g), which was used directly in the next step without purification. $^1$H NMR (250 MHz, CDCl$_3$) δ 7.07 (2H, d, J=7.5 Hz), 6.87 (2H, m), 4.42 (1H, s), 4.32 (1H, d, J=6.0 Hz), 4.03–3.93 (4H, m), 3.43–3.28 (1H, m), 3.12 (4H, br s), 0.48 (3H, s).

3,3-[1,2-Ethanediylbis(oxy)]-5α-hydroxy-17β-nitro-11β-[4-(N-piperidino)phenyl]estr-9-ene [A-1 (R$^1$=4-(N-piperidino)-, R$^6$=R$^7$=R$^{12}$=H)]. To a well-stirred solution of 69.3 g of the above crude bromide [A-1 (R$^1$=4-(N-piperidino)-, R$^7$=Br, R$^6$=R$^{12}$=H)] in 1.17 L of THF and 230 mL of water at room temperature was added 14.4 g (380 mmol) of NaBH$_4$ in small portions over a period of 1 h. After an additional 1 h, a solution of of 84.3 g (1.21 mol) of hydroxylamine hydrochloride in 585 mL of water was carefully added. After 15 min, the aqueous layer was separated and extracted three times with 116 mL of EtOAc. The combined organic solutions were washed three times with 116 mL of brine, dried over Na$_2$SO$_4$, filtered, and the solvent was removed under reduced pressure to afford a yellow foam (56.2 g). The material was taken up in a minimal amount of CH$_2$Cl$_2$ and chromatographed on silica gel (55% EtOAc in hexanes) to afford nitro intermediate A-1 (R$^1$=4-(N-piperidino)-, R$^6$=R$^7$=R$^{12}$=H) (33.3 g, 45% yield for 5 steps) as a yellow solid. $^1$H NMR (250 MHz, CDCl$_3$) δ 7.04 (2H, d, J=8.6 Hz), 6.81 (2H, d, J=8.8 Hz), 4.38(1H, s), 4.33 (1H, t, J=11 Hz), 4.23 (1H, d, J=6.6 Hz), 3.12–3.07 (4H, m), 2.71 (1H, d, J=13 Hz), 0.36 (3H, s).

17α-(2-Carbomethoxyethyl)-3,3-[1,2-ethanediylbis(oxy)]-5α-hydroxy-17β-nitro-11β-[4-(N-piperidino)phenyl]estr-9-ene [A-1 (R$^1$=4-(N-piperidino)-, R$^7$=—(CH$_2$)$_2$COOCH$_3$, R$^6$=R$^{12}$=H)]. To a mixture of 12.0 g (23.0 mmol) of nitro intermediate A-1 (R$^1$=4-(N-piperidino)-, R$^6$=R$^7$=R$^{12}$=H) in 65 mL of t-BuOH at room temperature was added 41.2 mL (460 mmol) of methyl acrylate, followed by the dropwise addition of 13.2 mL (30.0 mmol) of 40% w/w Triton B in MeOH. After 1 h at room temperature, 132 mL of saturated aqueous NH$_4$Cl solution and 132 mL of EtOAc were added. The aqueous layer was separated and extracted three times with 30 mL of EtOAc. The combined organic solutions were washed twice with 132 mL of brine, dried over Na$_2$SO$_4$, filtered, and the solvent was removed under reduced pressure. Chromatography on silica gel (60% EtOAc in hexanes) afforded nitroester A-1 (R$^1$=4-(N-piperidino)-, R$^7$=—(CH$_2$)$_2$COOCH$_3$, R$^6$=R$^{12}$=H) 11.8 g (85% yield). $^1$H NMR (250 MHz, CDCl$_3$) δ 7.04 (2H, d, J=8.6 Hz), 6.81 (2H, d, J=8.7 Hz), 4.35 (1H, s), 4.30 (1H, d, J=6.1 Hz), 4.03–3.93 (4H, m), 3.68 (3H, s), 3.11–3.07 (4H, m) 0.38 (3H, s).

3,3-[1,2-Ethanediylbis(oxy)]-5α-hydroxy-17α-(3-hydroxypropyl)-17β-nitro-11β-[4-(N-piperidino)phenyl]estr-9-ene [A-1 (R$^1$=4-(N-piperidino)-, R$^7$=—(CH$_2$),OH, R$^6$=R$^{12}$=H)]. To a solution of 8.13 g (13.3 mmol) of ester A-1 (R$^1$=4-(N-piperidino)-, R$^7$=—(CH$_2$)$_2$COOCH$_3$, R$^6$=R$^{12}$=H) in 145 mL of THF at 0° C. was added 67.0 mL (67 mmol of 1.0 M DIBAL-H in hexanes. After 15 min, 55 mL of saturated aqueous potassium sodium tartrate solution was added, thus causing a gel to form. After stirring the mixture at room temperature for 2 h, the gel had dissipated, giving a clear mixture. The aqueous layer was separated and extracted three times with EtOAc. The combined organic solutions were washed twice with brine, dried over Na$_2$SO$_4$, filtered, and the solvent was removed under reduced pressure to afford nitropropanol A-1 (R$^1$=4-(N-piperidino)-, R$^7$=—(CH$_2$)$_3$OH, R$^6$=R$^{12}$=H) as a yellow foam (7.83 g, 100% yield). $^1$H NMR (250 MHz, CDCl$_3$) δ 7.05 (2H, d, J=8.6 Hz), 6.81 (2H, d, J=8.7 Hz), 4.38 (1H, s), 4.29 (1H, d, J=6.4 Hz), 4.02–3.93 (4H, m), 3.68–3.50 (2H, m), 3.11–3.07 (4H, m), 2.90–2.75 (1H, m), 0.37 (3H, s).

17β-Amino-3,3-[1,2-ethanediylbis(oxy)]-5α-hydroxy-17α-(3-hydroxypropyl)-11β-[4-(N-piperidino)phenyl]estr-9-ene [A-4 (R$^1$=4-(N-piperidino)-, R$^7$=—(CH$_2$)$_3$OH, R$^6$=R$^{12}$=H)]. To a solution of 7.25 g (12.5 mmol) of nitropropanol A-1 (R$^1$=4-(N-piperidino)-, R$^7$=—(CH$_2$)$_3$OH, R$^6$=R$^{12}$=H) and 13.4 g (250 mmol) of NH$_4$Cl in 70 mL of EtOH, 70 mL of water, and 140 mL of THF at 70° C. was carefully added 49.0 g (749 mmol) of zinc dust (–325 mesh) over approximately 3 min. After the resulting mixture was stirred efficiently for 18 h, it was allowed to cool to room temperature then filtered through a pad of Celite with the aid of EtOAc. The filtrate was washed twice with brine, dried over N$_2$SO$_4$, filtered, and the solvent was removed under reduced pressure to afford aminopropanol A-4 (R$^1$=4-(N-piperidino)-, R$^7$=—(CH$_2$)$_3$OH, R$^6$=R$^{12}$=H) as a white amorphous solid (9.16 g), which was carried on to the next step without purification. $^1$H NMR (250 MHz, CDCl$_3$) δ 7.15 (2H, d, J=8.2 Hz), 6.85 (2H, d, J=8.3 Hz), 4.40–4.20 (2H, m), 4.05–3.82 (4H, m), 3.46 (2H, br s), 3.10 (4H, br s), 0.54 (3H, s).

17β-Amino-17α-(3-hydroxypropyl)-11β-[4-(N-piperidino)phenyl]estra-4,9-dien-3-one [A-6 (R$^1$=4-(N-piperidino)-, R$^7$=—(CH$_2$)$_3$OH, R$^6$=R$^{12}$=H)]. To a vigorously stirred milky-white mixture of 9.45 g (13.0 mmol assumed) of ketal A-4 (R$^1$=4-(N-piperidino)-, R$^7$=—(CH$_2$)$_3$OH, R$^6$=R$^{12}$=H), 575 mL of CH$_2$Cl$_2$, and 12 mL of water at 0° C. was added dropwise 16.6 mL (215 mmol) of trifluoroacetic acid, which gradually caused a light blue coloration which faded to pale yellow over approximately 15 min. After stirring vigorously for 2 h, saturated aqueous NaHCO$_3$ was carefully added and the mixture was allowed to gently stir at room temperature for 14 h. The mixture was extracted three times with EtOAc. The combined organic solutions were washed twice with brine, dried over Na$_2$SO$_4$, filtered, and the solvent was removed under reduced pressure to afford dienone A-6 (R$^1$=4-(N-piperidino)-, R$^7$=—(CH$_2$)$_3$OH, R$^6$=R$^{12}$=H) as a yellow foam (6.18 g, 74% adjusted yield over 3 steps) in a state of high purity by $^1$H NMR analysis. $^1$H NMR (250 MHz, CDCl$_3$) δ 7.04 (2H, d, J=8.6 Hz), 6.85 (2H, d, J=8.7 Hz), 5.76 (1H, s), 4.36 (1H, d, J=6.1 Hz), 3.62–3.42 (2H, m), 3.13–3.09 (4H, m), 0.54 (3H, s). MS m/z (rel inten) 488 (M$^+$, 21), 470 (37), 387 (100), 320 (25), 162 (52), 96 (35).

EXAMPLE 7

Synthesis of 17β-Hydroxylamino-17α-(3-hydroxypropyl)-11β-[4-(N-piperidino)phenyl]estra-4,9-dien-3-one [A-3 (R$^1$=4-(N-piperidino)-, R$^7$=—(CH$_2$)$_3$OH, R$^6$=R$^{12}$=H)]

3,3-[1,2-Ethanediylbis(oxy)]-5α-hydroxy-17β-hydroxylamino-17α-(3-hydroxypropyl)-11β-[4-(N-piperidino)phenyl]estr-9-ene [A-2 (R$^1$=4-(N-piperidino)-, R$^7$=—(CH$_2$)$_3$OH, R$^6$=R$^{12}$=H)]. To a solution of 4.34 g (7.47 mmol) of nitropropanol A-1 (R$^1$=4-(N-piperidino)-, R$^7$=—(CH$_2$)$_3$OH, R$^6$=R$^{12}$=H) and 840 mg (15.7 mmol) of NH$_4$Cl in 49 mL of EtOH, 49 mL of water, and 99 mL of THF at room temperature was added 4.40 g (67.2 mmol) of zinc dust (–325 mesh). After stirring efficiently for 2.5 h, the mixture was filtered through a pad of Celite with the aid of EtOAc.

The filtrate was washed twice with brine, dried over $N_2SO_4$, filtered, and the solvent was removed under reduced pressure. Chromatography on silica gel (6% MeOH in EtOAc) afforded starting nitropropanol A-1 ($R^1$=4-(N-piperidino)-, $R^7$=—$(CH_2)_3$OH, $R^6$=$R^{12}$=H) (420 mg, 10% recovery) and desired hydroxylamine propanol A-2 ($R^1$=4-(N-piperidino)-, $R^7$=—$(CH_2)_3$OH, $R^6$=$R^{12}$=H) (2.95 g, 70% yield). $^1$H NMR (250 MHz, CDCl$_3$) δ 7.07 (2H, d, J=8.5 Hz), 6.82 (2H, d, J=8.7 Hz), 5.29 (1H, br s), 4.35 (1H, s), 4.18–4.16 (1H, br s), 4.01–3.92 (4H, m), 3.75–3.65 (1H, m), 3.60–3.51 (1H, m), 3.10–3.05 (4H, m), 1.04–0.93 (1H, m), 0.57 (3H, s).

17β-Hydroxylamino-17α-(3-hydroxypropyl)-11β-[4-(N-piperidino)phenyl]estra-4,9-dien-3-one (A-3 ($R^1$=4-(N-piperidino)-, $R^7$=—$(CH_2)_3$OH, $R^6$=$R^{12}$=H)]. To a vigorously stirred mixture of 2.95 g (5.20 mmol) of hydroxylamine A-2 ($R^1$=4-(N-piperidino)-, $R^7$=—$(CH_2)_3$OH, $R^6$=$R^{12}$=H), 4.80 mL of water, and 230 mL of $CH_2Cl_2$ at 0° C. was added dropwise 6.50 mL (84.2 mmol) of trifluoroacetic acid. After stirring vigorously at 0° C. for 3 h, excess saturated aqueous NaHCO, solution was carefully added. After stirring at room temperature for 30 min, the mixture was extracted three times with EtOAc. The combined organic solution was washed twice with brine, dried over $Na_2SO_4$, filtered, and the solvent was removed under reduced pressure to afford a yellow foam (2.77 g). This material was combined with analogously prepared material (205 mg) in a minimal amount of $CH_2Cl_2$ and chromatographed on silica gel (5.5% MeOH in EtOAc) to afford a yellow foam (1.99 g). This was combined with similar additional material (393 mg) in a minimal amount of $CH_2Cl_2$ and chromatographed on silica gel (5.0% MeOH in EtOAc). Combination of the fractions determined to be >97% pure by HPLC analysis afforded dienone A-3 ($R^1$=4-(N-piperidino)-, $R^7$=—$(CH_2)_3$OH, $R^6$=$R^{12}$=H) (1.69 g, 52% adjusted yield). The majority of this material (1.68 g) was dried at 92° C. to 94° C. in vacuo for 38 h to provide solvent-free product by $^1$H NMR analysis and of >97% purity by HPLC analysis. $^1$H NMR (250 MHz, CDCl$_3$) δ 7.03 (2H, d, J=8.6 Hz), 6.84 (2H, d, J=8.7 Hz), 5.75 (1H, s), 5.21 (1H, br s, exchangeable with $D_2O$), 4.28 (1H, d, J=6.0 Hz), 3.78–3.74 (1H, m), 3.64–3.61 (1H, m), 3.10–3.02 (4H, m), 1.08–0.93 (1H, m), 0.64 (3H, s). MS m/z: LC-MS 505 (M+1); MS-MS 505 (M+1). Anal. Calcd. for $C_{32}H_{44}N_2O_3$: C, 76.15; H, 8.79; N, 5.55. Found: C, 75.90; H, 8.77; N, 5.50.

EXAMPLE 8

17β-(N-Formamido)-17α-[3-(formyloxy)propyl]-11β-[4-(N-piperidino)phenyl]estra-4,9-dien-3-one [A-8 ($R^1$=4-(N-piperidino)-, $R^7$=—$(CH_2)_3$OCHO, $R^{10}$=$R^6$=$R^{12}$=H)]

To a solution of 10.4 g (50.6 mmol) of dicyclohexylcarbodiimide in 28 mL of CHCl$_3$ at room temperature was added 101 mL (101 mmol) of 1.00 M formic acid in CHCl$_3$, causing a white precipitate. After 5 min, the mixture was added to a solution of 6.18 g (12.7 mmol) of amino alcohol A-6 ($R^1$=4-(N-piperidino)-, $R^7$=—$(CH_2)_3$OH, $R^6$=$R^{12}$=H)] and 12.4 mL (152 mmol) of pyridine in 55 mL of CHCl$_3$. After 15 min, a spatula tip of 4-dimethylaminopyridine was added. After 2.5 h, another spatula tip of 4-dimethylaminopyridine was added. An additional amount of a mixture of 2.60 g (12.7 mmol) of dicyclohexylcarbodiimide and 25.3 mL (25.3 mmol) of 1.00 M formic acid in CHCl, in 10 mL of CHCl$_3$ was stirred for 5 min, then added to the reaction mixture. After 1 h, the reaction mixture was diluted with 600 mL of diethyl ether and stirred efficiently for 12 h, then filtered through a pad of Celite with the aid of diethyl ether rinsings. The filtrate was concentrated by rotary evaporation under reduced pressure then in vacuo. The residue was stirred with 100 mL of EtOAc for 45 min, then the resulting solids were filtered through a pad of Celite with the aid of EtOAc rinsings. The filtrate was combined with a smaller batch of the desired crude product (0.688 mmol, in theory) which had been prepared similarly up to this point. The solvent was removed under reduced pressure. The residue was iteratively diluted three times with 30 mL of toluene and concentrated under reduced pressure by rotary evaporation (to remove pyridine) giving 8.42 g of an orange/yellow foam. The material was chromatographed twice on silica gel (85% EtOAc in hexanes) to afford 4.66 g of an amorphous yellow solid. A 1.63 g sample of this material was dried in vacuo for 21 h at 95° C., affording a yellow amorphous solid (1.51 g, 51% adjusted yield). The formate ester group was observed to be susceptible to slow cleavage in MeOH solution. Analysis by reverse phase analytical HPLC (C-18 column, YMC, inc.) showed >97% purity of the desired product, existing as two equilibrating forms. Verification of such interconversion was obtained by the separation of the individual forms by analytical HPLC, followed by their reinjection to provide virtually identical chromatograms. This behavior was also observed by two-dimensional TLC experiments, as well as in $^1$H NMR spectra (ca. 2:1 ratio). $^1$H NMR (250 MHz, CDCl$_3$ integration adjusted for ratio of major and minor forms) δ 8.03 (1H, s), 7.03 (2H, d, J=8.5 Hz), 6.83 (2H, d, J=8.6 Hz), 5.75 (1H, s), 5.32 (1H, s), 4.44–4.30 (1H, m), 4.25–4.15 (2H, m), 3.10 (4H, br s), 0.50 (3H, s); minor form: 8.14 (1H, d, J=12.4 Hz), 6.99 (2H, overlapping doublet), 5.95 (1H, d, J=12.4 Hz). Anal. Calcd. for $C_{34}H_{44}N_2O_4$: C, 74.97; H, 8.14; N, 5.14. Found: C, 74.72; H, 8.26; N, 5.07. MS m/z (rel inten) 544 (M$^+$, 25), 320 (23), 161 (100).

EXAMPLE 9

17β-(N-Formamido)-17α-(3-hydroxypropyl)-11β-[4-(N-piperidino)-phenyl]estra-4,9-dien-3-one [A-8 ($R^1$=4-(N-piperidino)-, $R^7$=—$(CH_2)_3$OH, $R^{10}$=$R^6$=$R^{12}$=H)]

To a mixture of 1.43 g (2.62 mmol) of formate ester A-8 ($R^1$=4-(N-piperidino)-, $R^7$=—$(CH_2)_3$OCHO, $R^{10}$=$R^6$=$R^{12}$=H)] and 24 mL of MeOH at room temperature with good stirring was added dropwise 0.48 mL of concentrated ammonium hydroxide, gradually causing the formation of a homogeneous solution. After 1.2 h, 24 mL of saturated aqueous ammonium chloride solution, 24 mL of water, and 24 mL of EtOAc were added. The aqueous layer was separated and extracted three times with EtOAc. The combined organic solutions were washed twice with brine, dried over $Na_2SO_4$, filtered, and the solvent was removed under reduced pressure to afford 1.35 g (100% yield) of product. The material was combined with 474 mg of analogously prepared crude product in a minimal amount of $CH_2Cl_2$ and chromatographed on silica gel (8% MeOH in EtOAc) to afford a yellow foam (1.59 g). The material was iterative diluted three times with 15 mL of $CH_2Cl_2$ and concentrated under reduced pressure by rotary evaporation to provide material free of all other solvents, by $^1$H NMR analysis. The material was dried at 95° C. for 23.5 h in vacuo to afford 1.36 g of essentially solvent-free desired formamido propanol A-8 ($R^1$=4-(N-piperidino)-, $R^7$=—$(CH_2)_3$OH, $R^{10}$=$R^6$=$R^{12}$=H) [1.45 g, 79% yield (adjusted for supplement)], in >97% purity by HPLC analysis. Equilibrating forms analogous to the above formamide A-8 ($R^1$=4-(N-piperidino), $R^7$=—$(CH_2)_3$OCHO, $R^{10}$=$R^6$=$R^{12}$=H) were similarly observed by analytical HPLC and $^1$H NMR (ca. 1:1 ratio). $^1$H NMR (250 MHz, CDCl$_3$ integration adjusted for ratio of forms) δ 8.12 (1H, d, J=12.3 Hz), 7.03 (2H, d, J=8.5 Hz), 6.83 (2H, d, 8.6 Hz), 6.39 (1H, d, J=12.9 Hz), 5.75 (1H, s), 4.40–4.31 (1H, m), 3.65–3.62 (2H, m), 3.10–3.08 (4H, m), 0.50 (3H, s); other form, partial: 8.01 (1H, s), 7.00 (2H, d, J=8.6 Hz), 5.39 (1H, s), 0.49 (3H, s). Anal. Calcd. for $C_{33}H_{44}N_2O_3 \cdot 0.25H_2O$: C, 76.04; H, 8.61; N, 5.37. Found: C, 75.95; H, 8.62; N, 5.38. MS m/z (rel inten) 516 (M+, 44), 387 (16), 320 (38), 161 (100).

EXAMPLE 10

Synthesis of 5'-Oxo-11β-[4-(N-piperidino)phenyl]-spiro[estra-4,9-dien-17β,2'-pyrrolidino]-3-one [B-3 ($R^1$=4-(N-piperidino)-, $R^6$=$R^{12}$=H)]

3,3-[1,2-Ethanediylbis(oxy)]-5α-hydroxy-5'-oxo-11β-[4-(N-piperidino)phenyl]-spiro[estr-9-ene-17β,2'-pyrrolidine] [B-2 ($R^1$=4-(N-piperidino)-, $R^6$=$R^{12}$=H)]. A solution of the nitro ester B-1 ($R^1$=4-(N-piperidino)-, $R^6$=$R^{12}$=H, R=$CH_3$) (3.13 g, 5.10 mmol) was prepared in 63 mL of 50% aqueous ethanol and 32 mL of THF. To this was added 1.93 g (73.4 mmol) of ammonium chloride and 20 g (306 mmol) of zinc dust. The reaction mixture was heated at 70° C. for 20 h. The reaction mixture was filtered through celite and the filtrate concentrated. The crude product was chromatographed on silica gel eluting with 6:3:1 ethyl acetate-hexane-methanol to give 1.97 g (70% yield) of pure B-2 ($R^1$=4-(N-piperidino)-, $R^6$=$R^{12}$=H): IR (solution, $CDCl_3$) 3495, 2995, 2855, 1685, 1506, 1438, 1384, 1226 $cm^{-1}$; $^1H$ NMR (250 MHz, $CDCl_3$) δ 7.03 (d, 2, J=8.5 Hz, ArH), 6.83 (d, 2, J=8.8 Hz, ArH), 5.57 (s, 1, NH), 4.39 (s, 1, $C_5OH$), 4.25 (d, 1, J=5.9 Hz, $C_{11\alpha}H$), 3.98–4.02 (m, 4, $(OCH_2)_2$), 3.09 (m, 4, $N(CH_2)_2$), 0.42 (s, 3, $C_{18}H$).

5'-Oxo-11β-[4-(N-piperidino)phenyl]-spiro[estra-4,9-dien-17β,2'-pyrrolidine]-3-one. [B-3 ($R^1$=4-(N-piperidino)-, $R^6$=$R^{12}$=H)]. To a solution of 120 mg (0.23 mmol) of B-2 ($R^1$=4-(N-piperidino)-, $R^6$=$R^{12}$=H) in 2.5 mL of $CH_2Cl_2$ was added 0.1 mL of water and the mixture was cooled to 0° C. To the solution was added about 0.5 mL of trifluoroacetic acid (TFA) dropwise. The reaction was stirred at 0° C. for 1 h. The reaction was quenched with saturated sodium bicarbonate solution, and extracted with $CH_2Cl_2$. The $CH_2Cl_2$ layer was washed with water, followed by brine and dried over anhydrous $MgSO_4$. The dried solution was then filtered and concentrated under vacuum. The crude product was chromatographed on silica gel using 5:5:1 methylene chloride-hexane-methanol as eluant to give 79 mg (76% yield) of pure B-3 ($R^1$=4-(N-piperidino)-, $R^6$=$R^{12}$=H). $^1H$ NMR (250 MHz, $CDCl_3$) δ 6.99 (d, 2, J=8.7 Hz, ArH), 6.64 (d, 2, J=8.8 Hz, ArH), 5.79 (s, 1, NH), 5.77 (s, 1, $C_4H$), 4.36 (d, 1, J=6.4 Hz, $C_{11\alpha}H$), 3.12 (m, 4, $N(CH_2)_2$), 0.49 (s, 3, $C_{18}H$); mass spectrum, m/z (rel intensity) 484(75), 374 (5), 320(16), 213(6), 174(17), 161(100); Anal. Calcd for $C_{32}H_4N_2O_2$: C, 79.30; H, 8.32; N, 5.78. Found: C, 79.12; H, 8.26; N, 5.72.

EXAMPLE 11

Synthesis of 11β-[4-(N,N-Dimethylamino)phenyl]-1'-hydroxy-5'-methyl-spiro[estra-4,9-dien-17β,2'-pyrrolidine]-3-one [C-3 ($R^1$=4-($Me_2N$—, $R^6$=$R^{12}$=H, $R^{13}$=$CH_3$)]

1',5α-Dihydroxy-11β-[4-(N,N-dimethylamino)phenyl]-3,3-[1,2-ethanediylbis(oxy)]-5'-methyl-spiro[estr-9-ene-17β,2'-pyrrolidine] [C-2 ($R^1$=4-$Me_2N$—)-, $R^6$=$R^{12}$=H, $R^{13}$=$CH_3$]. To a stirred solution of C-1 ($R^1$=4-$Me_2N$—, $R^6$=$R^{12}$=H, $R^{13}$=$CH_3$) (200 mg, 0.38 mmol) and (3.58 mmol) of $NaBH_3CN$ in 4 mL of methanol, was added 0.5 mL of AcOH. The reaction was stirred at room temperature for 2 h. The reaction was quenched with saturated $NH_4Cl$ solution and extracted with $CH_2Cl_2$. The organic layer was washed with water, followed by brine and dried over anhydrous $Na_2SO_4$. The organic layer was filtered and concentrated to give crude C-2 ($R^1$=4-$Me_2N$—, $R^6$=$R^{12}$=H, $R^{13}$=$CH_3$) which was used without further purification in the next step. $^1H$ NMR (250 MHz, $CDCl_3$) δ 7.06 (d, 2, J=8.7 Hz, ArH), 6.64 (d, 2, J=8.7 Hz, ArH), 4.35 (s, 1, C, OH), 4.19(d, 1, J=6.2 Hz, $C_{11\alpha}H$), 3.98–4.02 (m, 4, $(OCH_2)_2$), 2.88 (s, 6, $N(CH_3)_2$), 1.19 (d, 3, J=6.5 Hz $HONCHCH_3$), 0.62 (s, 3, $C_{18}H$).

11β-[4-(N,N-Dimethylamino)phenyl]-1'-hydroxy-5'-methyl-spiro[estra-4,9-dien-17β,2'-pyrrolidine]-3-one [C-3 ($R^1$=4-$Me_2N$—, $R^6$=$R^{12}$=H, $R^{13}$=$CH_3$)]. To a solution of 200 mg (0.38 mmol) of C-2 ($R^1$=4-$Me_2N$—, $R^6$=$R^{12}$=H, $R^{13}$=$CH_3$) in 2.0 mL $CH_2Cl_2$, was added 0.1 mL of water and the mixture was cooled to 0° C. To the cooled solution was added about 0.5 mL of TFA dropwise. The reaction was stirred at 0° C. for 1 h. The reaction was then quenched with saturated sodium bicarbonate solution, and extracted with $CH_2Cl_2$. The $CH_2Cl_2$ layer was washed with water, followed by brine and dried over anhydrous $Na_2SO_4$. The dried solution was filtered and concentrated under vacuum. The crude product was chromatographed on silica gel using 3:1 ethyl acetate-hexane as eluant to give 114 mg (65% yield) of pure C-3 ($R^1$=4-$Me_2N$—, $R^6$=$R^{12}$=H, $R^{13}$=$CH_3$). $^1H$ NMR (250 MHz, $CDCl_3$) δ 7.02 (d, 2, J=8.6 Hz, ArH), 6.65 (d, 2, J=8.7 Hz, ArH), 5.74 (s, 1, $C_4H$), 4.30 (d, 1, J=6.8 Hz, $C_{11\alpha}H$), 2.89 (s, 6, $N(CH_3)_2$), 1.19 (d, 3, J=6.4 Hz, HONCHCH_3), 0.69 (s, 3, $C_{18}CH_3$); mass spectrum, m/z (rel intensity) 459(8), 458(23), 442(31), 280(12), 134(100), 121 (33), 96(7); Anal. Calcd. for $C_{30}H_{40}N_2O_2 \cdot 0.25H_2O$: C, 77.45; H, 8.83; N, 5.61. Found: C, 77.46; H, 8.78; N, 6.02.

EXAMPLE 12

Synthesis of 11β-[4-(N,N-Dimethylamino)phenyl]-1'-hydroxy-spiro[estra-4,9-dien-17β,2'-pyrrolidine]-3-one [C-3 ($R^1$=4-$Me_2N$—, $R^6$=$R^{12}$=H, $R^{13}$=H)]

1',5α-Dihydroxy-11β-[4-N,N-dimethylamino)phenyl]-3,3-[1,2-ethanediylbis(oxy)]-spiro[estr-9-ene-17β,2'-pyrrolidine] [C-2 ($R^1$=4-$Me_2N$—, $R^6$=$R^{12}$=H, $R^{13}$=H)]. To a stirred solution of C-1 ($R^1$=4-$Me_2N$—, $R^6$=$R^{12}$=H, $R^{13}$=H) (200 mg, 0.39 mmol) and 234 mg (3.77 mmol) of $NaBH_3CN$ in 5 mL of methanol was added 0.5 mL of AcOH. After stirring at room temperature for 2 h, the reaction was quenched with saturated $NH_4Cl$ solution and extracted with $CH_2Cl_2$. The organic layer was washed with water, followed by brine and dried over anhydrous $Na_2SO_4$. The organic layer was filtered and concentrated to give the crude product which was used without further purification in the next step. $^1H$ NMR (250 MHz, $CDCl_3$) δ 7.04 (d, 2, J=8.7 Hz, ArH), 6.64 (d, 2, J=8.8 Hz, ArH), 4.37 (s, 1, $C_5OH$), 416 (d, 1, J=7.4 Hz, $C_{11\alpha}H$), 3.92–4.02 (m, 4, $(OCH_2)_2$), 2.90 (s, 6, $N(CH_3)_2$), 0.64 (s, 3, $C_{18}H$).

11β-[4-N,N-Dimethylamino)phenyl]-1'-hydroxy-spiro[estra-4,9-dien-17β,2'-pyrrolidine]-3-one [C-3 ($R^1$=4-

Me$_2$N—, R$^6$=R$^{12}$=H, R$^{13}$=H)]. To a solution of 200 mg (0.39 mmol) of C-2 (R$^1$=4-Me$_2$N—, R$^6$=R$^{12}$=H, R$^{13}$=H) in 5.0 mL of CH$_2$Cl$_2$ was added 0.1 mL of water and the mixture was cooled to 0° C. To the cooled solution was added about 0.5 mL of TFA dropwise. After stirring for 1 h at 0° C., the reaction was quenched with saturated sodium bicarbonate solution, and extracted with CH$_2$Cl$_2$. The CH$_2$Cl$_2$ layer was washed with water, followed by brine and dried over anhydrous Na$_2$SO$_4$. The dried solution was filtered and concentrated under vacuum. The crude product was chromatographed on silica gel using 3:1 ethyl acetate-hexane as eluant to give 115 mg (65% yield) of pure C-3 (R$^1$=4-Me$_2$N—, R$^6$=R$^{12}$=H, R$^{13}$=H). $^1$H NMR (250 MHz, CDCl$_3$) δ 7.00 (d, 2, J=8.7 Hz, ArH), 6.65 (d, 2, J=8.8 Hz, ArH), 5.75 (s, 1, C$_4$H), 4.29 (d, 1, J=6.7 Hz, C$_{11α}$H), 2.91 (s, 6, N(CH$_3$)$_2$), 0.66 (s, 3, C$_{18}$H); mass spectrum, m/z (rel intensity) 446(11), 428(66), 347(82), 280(27), 226(31), 134(80), 121(87), 96(100), 83(42); Anal. Calcd for C$_{29}$H$_{38}$N$_2$O$_2$.0.25H$_2$O: C, 77.44; H, 8.84; N, 5.84. Found: C, 77.20; H, 8.60; N, 6.21.

The biological activity of the compounds of this invention was examined by means of in vitro and in vivo tests.

Receptor Binding:

The affinity of the compounds for the human progesterone hormone receptor was determined by standard procedures similar to those that have been described in Horwitz, et al., *Cell*, 28: 633–42 (1982) and Mockus, et al., *Endocrinology*, 110: 1564–71 (1982). The receptor was obtained in cytosol from human T-47D breast cells and [$^3$H]-R5020 was used as the radioligand. T47D cells (1 billion/ml) were homogenized in TEDG buffer (10 mM Tris, 1.5 mM EDTA, 1 mM dithiothreitol, 1 mM sodium molybdate, and 10% glycerol) using a Dounce pestle A, and the homogenate was centrifuged at 34,000×g for 1 hour. The supernatant was stored at −80° C. An aliquot of receptor preparation was combined with test compound, 0.4 nM [$^3$H]-R5020, and TEDG buffer to a final volume of 150 μL and incubated for 4 hours at 4° C. in microtiter plates. At the end of incubation 40 μL 40% polyethylene glycol and 15 μL 1% human gamma globulin was added to the incubate and the contents of each well were harvested onto double thick B filter mats (Wallac LKB) using a TomTec harvester. A film of Meltilux scintillant wax was applied to the dried filter mats and the mats were counted in a scintillation counter to determine inhibition of [$^3$H]-R5020 binding. Data are expressed as IC$_{50}$ values, i.e., the concentration of compound that inhibits radioligand binding by 50%.

Table 1 shows that compounds of the present invention bind strongly to the progestin receptor but with varying degrees of affinity.

Animal tests were also performed to further characterize the biological activity of the compounds of the invention.

Determination of Progestational and Antiprogestational Activity In Vivo:

Progestational activity and antiprogestational activity were determined in rabbits by means of the McGinty test (test compound alone, procedure of McGinty et al., *Endocrinology*, 24: 829–832 (1939)) or anti-McGinty test (test compound plus progesterone, procedure of Tamara et al., *Jpn. J. Fertil. Steril.* 24: 48–81 (1979)). Results were scored according to McPhail (McPhail, *J. Physiol.*, 83: 146 (1934)). These are standard procedures well-known to those skilled in the art. The results of these assays are shown in Tables 2 (agonist activity) and 3 (antagonist activity). Most of the compounds shown exhibited antiprogestational activity. Some compounds were extremely potent in this regard. For example, compounds I (R$^1$=4-Me$_2$N—C$_6$H$_4$, X=O, R$^6$=R$^8$=R$^{12}$=H, R$^7$=CH$_3$CC, R$^9$=CHO) and I ((R$^1$=4-Me$_2$N—C$_6$H$_4$, X=O, R=R=R=H, R=CH$_3$CC, R$^9$=OH) were completely effective in blocking the action of progesterone at a dose of only 0.3 μg in the anti-McGinty assay (Table 3). However the latter compound also exhibited some progestational (agonist) activity at a high doses in the McGinty assay (Table 2) and at the highest dose in the anti-McGinty assay. Thus a variety of agonist and antagonist properties may be found among compounds of this invention.

Anti-estrogenic Activity:

Certain of the compounds exhibited non-competitive anti-estrogenic activity of the type reported for mifepristone, for example by Wolf et al. (Fertil. Steril. 52: 1055–1060 (1989). Surprisingly they exhibited this activity in spite of the fact that they do not have the 17β-hydroxyl substituent characteristic of both mifepristone and estrogens such as estradiol but instead have 17β-nitrogen substituents. Thus, when immature female rabbits were administered 11β-(4-(N,N-dimethylamino)phenyl)-17β-(N-formamido)-17α-(1-propynyl)estra-4,9-dien-3-one orally at 10 mg/day concurrently with 5 μg of estradiol per day and the uteri were removed and weighed, the uterine weight, which was raised from 216.7±37.2 (S.E.) mg with no estradiol to 1337±105 mg with estradiol alone, was reduced to 716±96.6 mg.

TABLE 1

Receptor Binding Affinity

| Structure | R$^1$ | R$^{12}$ | X | R$^6$ | R$^7$ | R$^8$ | R$^9$ | R$^{13}$ | R$^{14}$ | Relative Binding Affinity hPR IC$_{50}$(nM) |
|---|---|---|---|---|---|---|---|---|---|---|
| Progesterone | | | | | | | | | | 3.3 |
| I | 4-Me$_2$N | H | O | H | —CC—CH$_3$ | H | OH | — | — | 14.3 |
| I | 4-Me$_2$N | H | O | H | —CC—CH$_3$ | CH$_3$ | OH | — | — | 7.1 |
| I | 4-Me$_2$N | H | O | H | —CC—CH$_3$ | H | H | — | — | 8.3 |
| I | 4-Me$_2$N | H | O | H | —CC—CH$_3$ | H | CH$_3$C(=O) | — | — | 1.3 |
| I | 4-Me$_2$N | H | O | H | —CC—CH$_3$ | H | HC(=O) | — | — | 0.7 |
| II | 4-Me$_2$N | H | O | H | — | H | OH | CH$_3$ | H | 5.2 |
| II | 4-Me$_2$N | H | O | H | — | H | OH | H | H | 3.5 |

TABLE 2

Progestational Activity

McGinty Assay (Agonist)

| Structure | $R^1$ | $R^2$ | X | $R^6$ | $R^7$ | $R^8$ | $R^9$ | $R^{13}$ | $R^{14}$ | Dose (Micrograms) | | |
|---|---|---|---|---|---|---|---|---|---|---|---|---|
| | | | | | | | | | | 0.3 | 3 | 30 |
| | | | | | | | | | | McPhail Index | | |
| Vehicle | | | | | | | | | | 0 | | |
| Progesterone | | | | | | | | | | 2.45 ± 0.14 | | |
| I | 4-Me$_2$N | H | O | H | —CC—CH$_3$ | H | OH | — | — | 0 ± 0 | 0 ± 0 | 0.7 ± 0.0 |
| I | 4-Me$_2$N | H | O | H | —CC—CH$_3$ | CH$_3$ | OH | — | — | 0 ± 0 | 0 ± 0 | 0 ± 0 |
| I | 4-Me$_2$N | H | O | H | —CC—CH$_3$ | H | H | — | — | 0 ± 0 | 0 ± 0 | 0 ± 0 |
| I | 4-Me$_2$N | H | O | H | —CC—CH$_3$ | H | CH$_3$C(=O) | — | — | 0 ± 0 | 0 ± 0 | 0 ± 0 |
| I | 4-Me$_2$N | H | O | H | —CC—CH$_3$ | H | HC(=O) | — | — | 0 ± 0 | 0 ± 0 | 0 ± 0 |
| II | 4-Me$_2$N | H | O | H | — | | H | OH | CH$_3$ | H | 0 ± 0 | 0 ± 0 | 0 ± 0 |
| II | 4-Me$_2$N | H | O | H | — | | H | OH | H | H | 0 ± 0 | 0 ± 0 | 0 ± 0 |

TABLE 3

Antiprogestational Activity

Anti-McGinty

Assay (Antagonist)

| Structure | $R^1$ | $R^{12}$ | X | $R^6$ | $R^7$ | $R^8$ | $R^9$ | $R^{13}$ | $R^{14}$ | Dose (Micrograms) | | |
|---|---|---|---|---|---|---|---|---|---|---|---|---|
| | | | | | | | | | | 0.3 | 3 | 30 |
| | | | | | | | | | | McPhail Index | | |
| Vehicle | | | | | | | | | | 0 | | |
| RJW 1719 | | | | | | | | | | 2.45 ± 0.14 | | |
| I | 4-Me$_2$N | H | O | H | —CC—CH$_3$ | H | OH | — | — | 0 ± 0 | 0 ± 0 | 2.5 ± 0.4 |
| I | 4-Me$_2$N | H | O | H | —CC—CH$_3$ | CH$_3$ | OH | — | — | 2.0 ± 0.2 | 0 ± 0 | 0 ± 0 |
| I | 4-Me$_2$N | H | O | H | —CC—CH$_3$ | H | H | — | — | 1.6 ± 0.3 | 0.2 ± 0.1 | 0 ± 0 |
| I | 4-Me$_2$N | H | O | H | —CC—CH$_3$ | H | CH$_3$C(=O) | — | — | 1.8 ± 0.3 | 0.1 ± 0.1 | 0 ± 0 |
| I | 4-Me$_2$N | H | O | H | —CC—CH$_3$ | H | HC(=O) | — | — | 0 ± 0 | 0 ± 0 | 0 ± 0 |
| II | 4-Me$_2$N | H | O | H | — | | H | OH | CH$_3$ | H | 2.1 ± 0.3 | 2.4 ± 0.4 | 0.7 ± 0.4 |
| II | 4-Me$_2$N | H | O | H | — | | H | OH | H | H | 2.7 ± 0.0 | 2.3 ± 0.5 | 0.07 ± 0.07 |

Obviously, numerous modifications and variations of the present invention are possible in light of the above teachings. It is therefore to be understood that within the scope of the appended claims, the invention may be practiced otherwise than as specifically described herein.

What is claimed is:

1. The steroid structure I

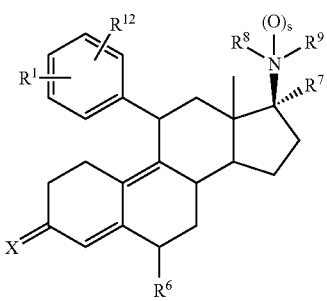

(I)

$R^1$-Ph is 4-aminophenyl, 4-(N-methylamino)phenyl, 4-(N,N-dimethylamino)phenyl, 4-(N-piperidino)phenyl, 4-(N-pyrrolidino)phenyl, or 4-(N-morpholino)phenyl;
$R^{12}$ is H or halo;
X is O or NOH;
$R^6$ is H;
$R^7$ is 1-propynyl, 3,3,3-trifluropropyn-1-yl;
s is 0 or 1;
$R^8$ is H; and
$R^9$ is CHO or CH$_3$CO.

2. A method of therapeutically treating the activity of progesterone comprising administering a therapeutically effective amount of the compound of claim 1 to a patient in need thereof for a therapeutic purpose.

3. The method of claim 2, wherein said therapeutic purpose is the treatment of endometriosis or uterine fibroids.

4. The method of claim 2, wherein said therapeutic purpose is cervical ripening preparatory to labor and delivery of offspring.

5. The method of claim 2, wherein said therapeutic purpose is the control or regulation of fertility.

6. The method of claim 2, wherein said therapeutic purpose is hormone replacement therapy.

7. The steroid compound 11β-(4-(N,N-dimethylamino)phenyl)-17β-(N-formamido)-17α-(1-propynyl)estra-4,9-dien-3-one.

8. A method of therapeutically treating the activity of progesterone comprising administering a therapeutically effective amount of the compound of claim 7 to a patient in need thereof for a therapeutic purpose.

9. The method of claim 8, wherein said therapeutic purpose is the treatment of endometriosis or uterine fibroids.

10. The method of claim 8, wherein said therapeutic purpose is cervical ripening preparatory to labor and delivery of offspring.

11. The method of claim 8, wherein said therapeutic purpose is the control or regulation of fertility.

12. The method of claim 8, wherein said therapeutic purpose is hormone replacement therapy.

13. The steroid compound 17β-(N-formamido)-11β-(4-(N-piperidino)phenyl)-17α-(1-propynyl)estra-4,9-dien-3-one.

14. A method of therapeutically treating the activity of progesterone comprising administering a therapeutically effective amount of the compound of claim 13 to a patient in need thereof for a therapeutic purpose.

15. The method of claim 14, wherein said therapeutic purpose is the treatment of endometriosis or uterine fibroids.

16. The method of claim 14, wherein said therapeutic purpose is cervical ripening preparatory to labor and delivery of offspring.

17. The method of claim 14, wherein said therapeutic purpose is the control or regulation of fertility.

18. The method of claim 14, wherein said therapeutic purpose is hormone replacement therapy.

* * * * *

UNITED STATES PATENT AND TRADEMARK OFFICE
CERTIFICATE OF CORRECTION

PATENT NO. : 7,018,991 B2  Page 1 of 1
APPLICATION NO. : 10/611785
DATED : March 28, 2006
INVENTOR(S) : C. Edgar Cook et al.

It is certified that error appears in the above-identified patent and that said Letters Patent is hereby corrected as shown below:

Column 8, line 60, "17$\beta$-amino-11 -(4-(N-peperidino)phenyl)"
  should read -- 17$\beta$-amino-1 1$\beta$-(4-(N-peperidino)phenyl) --.

Column 14, line 36, "*Other Antiproizestins*," should read -- *Other Antiprogestins*, --;
  line 53, "pyrole]-5$\alpha$-ols" should read -- pyrrole]-5$\alpha$-ols --.

Column 17, line 36, "2.54 (3H, s), 0.51 (3H, s)."
  should read -- 2.54 (3H, s), 1.96 (3H, s), 0.51 (3H, s). --.

Column 22, line 56, "3.44-3.39 (2H,s)."
  should read -- 3.44-3.39 (2H, m), 0.49 (3H, s). --.

Column 23, line 59, "$R^7$ = —(CH$_2$),OH," should read -- $R^7$= —(CH$_2$)$_3$OH, --.

Column 27, line 54, "$C_{32}H_4N_2O_2$:" should read -- $C_{32}H_{40}N_2O_2$: --.

Column 28, line 12, "4.35 (s, 1, C," should read --4.35 (s, 1, $C_5$ --;
  line 63, "416 (d, l," should read --4.16 (d, 1, --.

Column 30, line 23, "R=R=R=H, R=CH$_3$CC,"
  should read -- $R^6$=$R^8$=$R^{12}$=H, $R^7$=CH$_3$CC, --.

Column 31, line 42, "1. The steroid structure I" should read -- 1. A steroid structure I --.

Signed and Sealed this

Twenty-sixth Day of December, 2006

JON W. DUDAS
*Director of the United States Patent and Trademark Office*